United States Patent
Avalos et al.

(10) Patent No.: US 11,041,161 B2
(45) Date of Patent: Jun. 22, 2021

(54) METABOLIC FLUX BIOSENSOR

(71) Applicants: Whitehead Institute for Biomedical Research, Cambridge, MA (US); Massachusetts Institute of Technology, Cambridge, MA (US)

(72) Inventors: Jose Luis Avalos, Arlington, MA (US); Gerald Fink, Chestnut Hill, MA (US); Gregory Stephanopoulos, Winchester, MA (US)

(73) Assignees: Whitehead Institute for Biomedical Research, Cambridge, MA (US); Massachusetts Institute of Technology, Cambridge, MA (US)

( * ) Notice: Subject to any disclaimer, the term of this patent is extended or adjusted under 35 U.S.C. 154(b) by 46 days.

(21) Appl. No.: 15/110,158

(22) PCT Filed: Jan. 8, 2015

(86) PCT No.: PCT/US2015/010665
§ 371 (c)(1),
(2) Date: Jul. 7, 2016

(87) PCT Pub. No.: WO2015/106004
PCT Pub. Date: Jul. 16, 2015

(65) Prior Publication Data
US 2016/0326535 A1  Nov. 10, 2016

Related U.S. Application Data

(60) Provisional application No. 61/925,176, filed on Jan. 8, 2014.

(51) Int. Cl.
| | |
|---|---|
| *C12N 15/81* | (2006.01) |
| *C12P 7/16* | (2006.01) |
| *C12Q 1/6897* | (2018.01) |
| *C12P 13/04* | (2006.01) |
| *C12P 7/06* | (2006.01) |
| *C12N 9/10* | (2006.01) |
| *C07K 14/395* | (2006.01) |
| *G01N 33/50* | (2006.01) |

(52) U.S. Cl.
CPC ............ *C12N 15/81* (2013.01); *C07K 14/395* (2013.01); *C12N 9/1025* (2013.01); *C12P 7/06* (2013.01); *C12P 7/16* (2013.01); *C12P 13/04* (2013.01); *C12Q 1/6897* (2013.01); *G01N 33/5038* (2013.01); *Y02E 50/10* (2013.01)

(58) Field of Classification Search
None
See application file for complete search history.

(56) References Cited

U.S. PATENT DOCUMENTS

| | | | | |
|---|---|---|---|---|
| 4,870,159 A | * | 9/1989 | Friden | C07K 14/395 435/116 |
| 7,951,923 B2 | * | 5/2011 | Lukyanov | C07K 14/43595 435/69.1 |
| 2012/0184465 A1 | * | 7/2012 | Picataggio | C12N 15/1027 506/17 |
| 2013/0244243 A1 | | 9/2013 | Matsuyama et al. | |

OTHER PUBLICATIONS

Hu et al. The *Saccharomyces cerevisiae* Leu3 Protein Activates Expression of GDH1, a Key Gene in Nitrogen Assimilation. Jan. 1995. Molecular and Cellular Biology. vol. 15, No. 1, pp. 52-57.*

Iraqui et al., Transcriptional induction by aromatic amino acids in *Saccharomyces cerevisiae*. Mol Cell Biol. May 1999;19(5):3360-71.

Lee et al., Interplay of Aro80 and GATA activators in regulation of genes for catabolism of aromatic amino acids in *Saccharomyces cerevisiae*. Mol Microbiol. Jun. 2013;88(6):1120-34. doi: 10.1111/mmi.12246.

Poulou et al., Development of a chromosomally integrated metabolite-inducible Leu3p-alpha-IPM "off-on" gene switch. PLoS One. Aug. 31, 2010;5(8):e12488. doi:10.1371/journal.pone.0012488.

* cited by examiner

*Primary Examiner* — Channing S Mahatan
(74) *Attorney, Agent, or Firm* — Wolf, Greenfield & Sacks, P.C.

(57) ABSTRACT

Metabolic flux biosensors are provided herein, as are related compositions and methods useful for, inter alia, identifying factors which increase the production of metabolites and/or end products of metabolic pathways, and for the production of inter alia, metabolites and/or end products of metabolic pathways.

20 Claims, 21 Drawing Sheets

Specification includes a Sequence Listing.

FIGURE 4
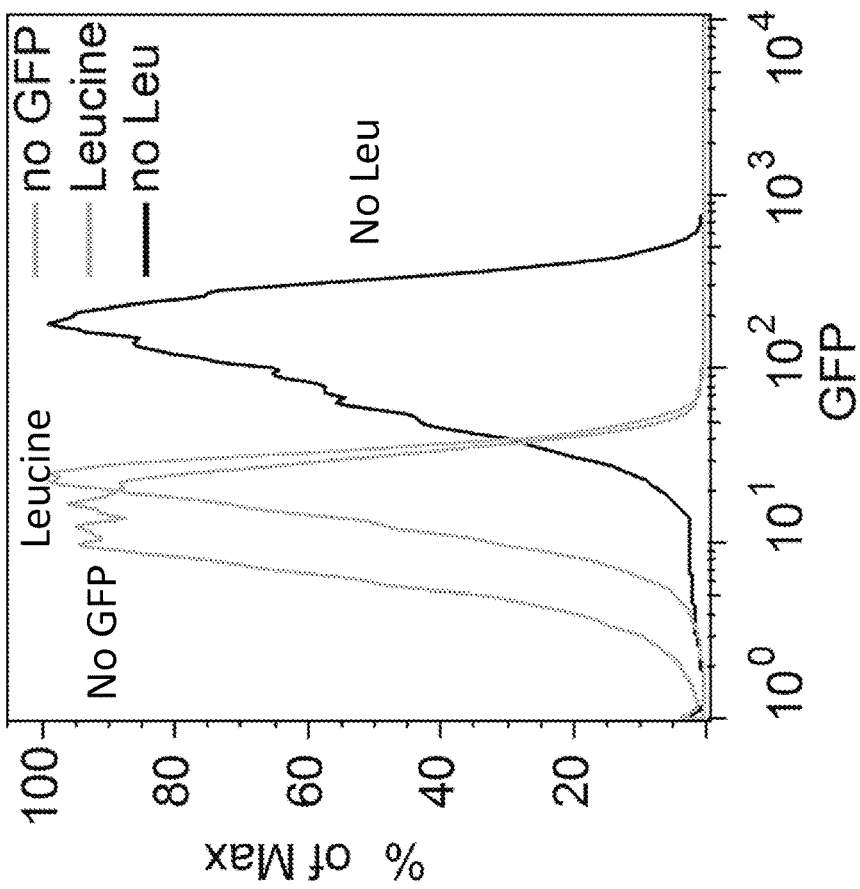
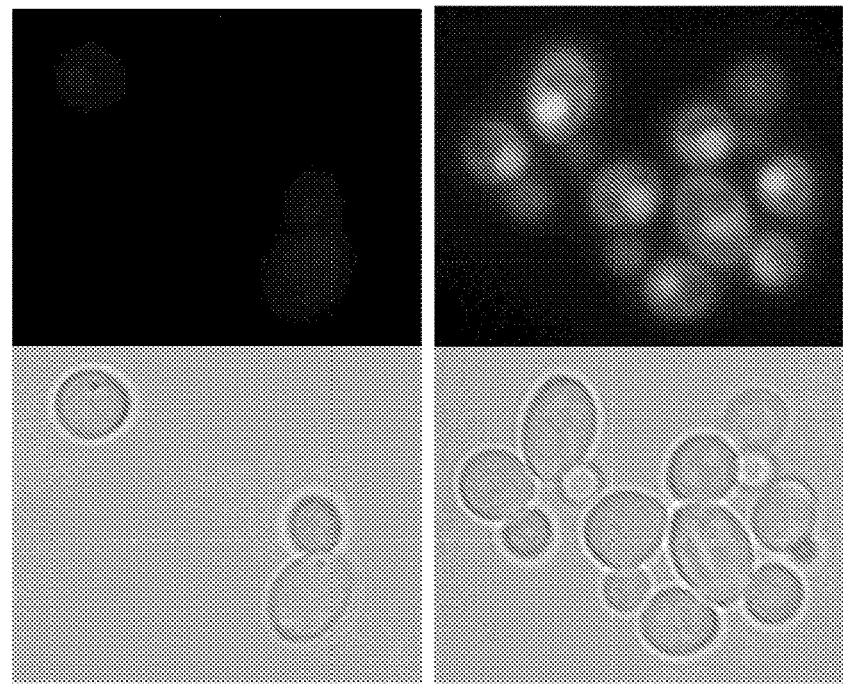
Low throughput | High throughput

FIGURE 7
LEU1 ORF YFP Replacement Construct A
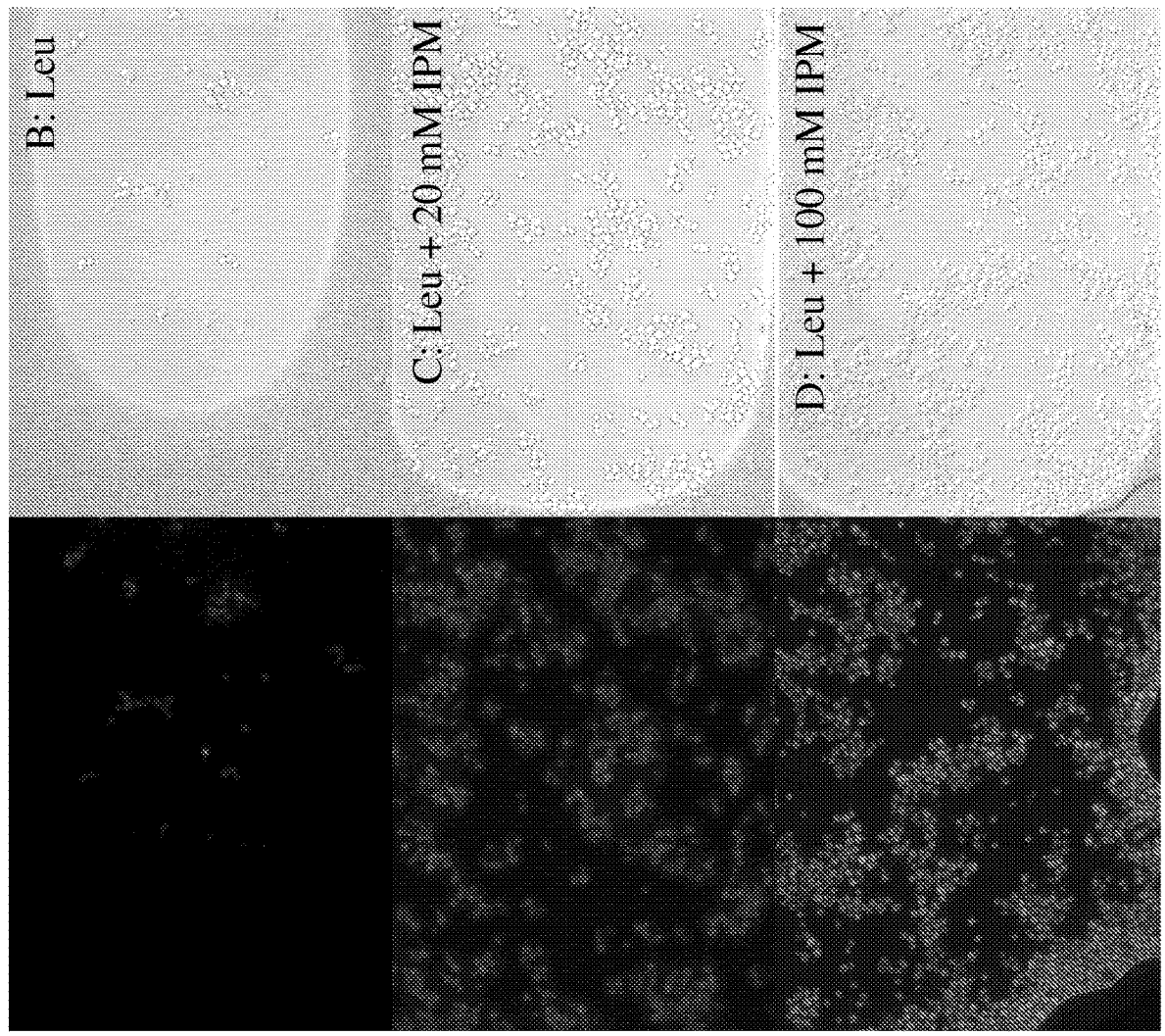
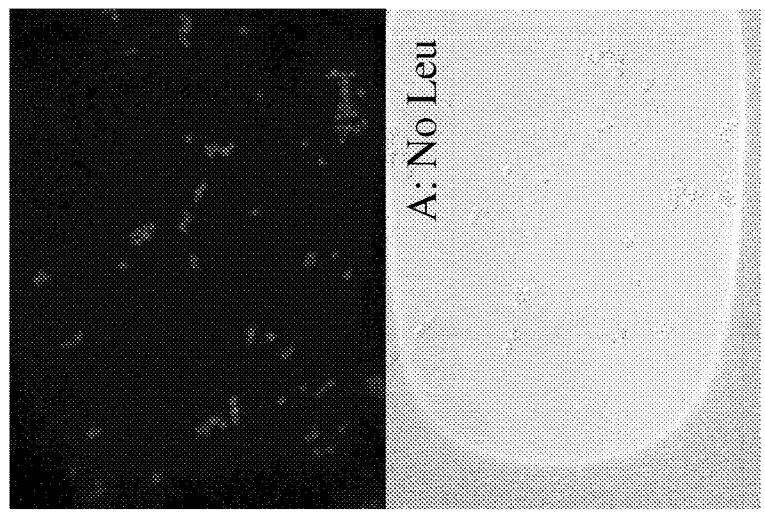

FIGURE 11
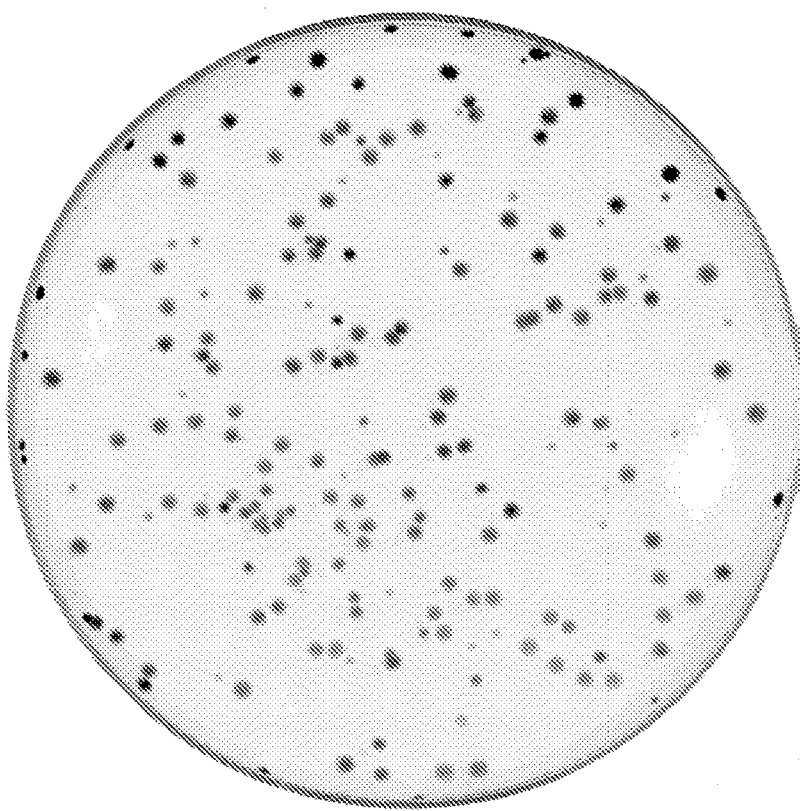
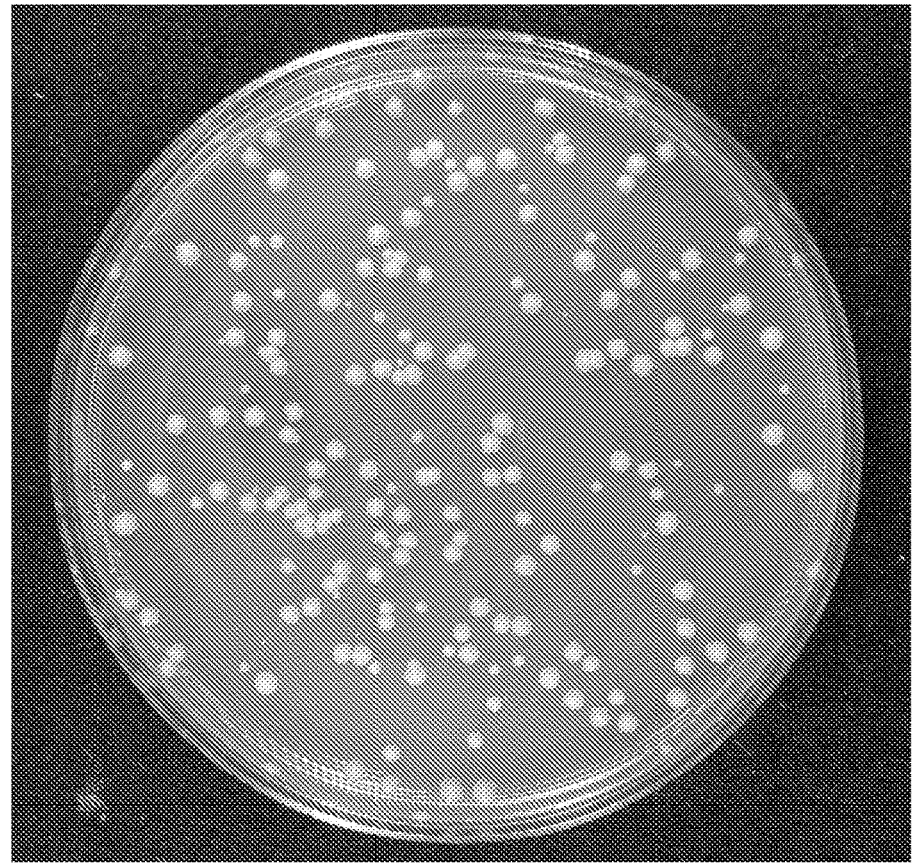

FIGURE 14

| Metabolic inducer | Activator |
|---|---|
| proline | Put3p |
| galactose | Gal4p |
| orotic acid | Ppr1p |
| α-isopropylmalate | Leu3p |
| α-aminoadipate semialdehyde | Lys14p |
| arginine | Arg81p |
| benzoic acid | War1p |
| 5'-phosphoribosyl-5-aminoimidazole-4-N-succinocarboxamide | Bas1p |

Applications:
- Find new genes/mutations that enhance heavy alcohol production
- Screen colonies in transformation reactions
- Link to auxotrophic marker to select for high producers
- Control engineered pathways ILV Pathway is OFF     ILV Pathway is ON

SEQUENCE LISTING

<160> NUMBER OF SEQ ID NOS: 3

<210> SEQ ID NO 1
<211> LENGTH: 619
<212> TYPE: PRT

<213> ORGANISM: Saccharomyces cerevisiae

<400> SEQUENCE: 1

```
Met Val Lys Glu Ser Ile Ile Ala Leu Ala Glu His Ala Ala Ser Arg
1               5                   10                  15

Ala Ser Arg Val Ile Pro Pro Val Lys Leu Ala Tyr Lys Asn Met Leu
            20                  25                  30

Lys Asp Pro Ser Ser Lys Tyr Lys Pro Phe Asn Ala Pro Lys Leu Ser
        35                  40                  45

Asn Arg Lys Trp Pro Asp Asn Arg Ile Thr Arg Ala Pro Arg Trp Leu
    50                  55                  60

Ser Thr Asp Leu Arg Asp Gly Asn Gln Ser Leu Pro Asp Pro Met Ser
65                  70                  75                  80

Val Glu Gln Lys Lys Glu Tyr Phe His Lys Leu Val Asn Ile Gly Phe
                85                  90                  95

Lys Glu Ile Glu Val Ser Phe Pro Ser Ala Ser Gln Thr Asp Phe Asp
            100                 105                 110

Phe Thr Arg Tyr Ala Val Glu Asn Ala Pro Asp Asp Val Ser Ile Gln
        115                 120                 125

Cys Leu Val Gln Ser Arg Glu His Leu Ile Lys Arg Thr Val Glu Ala
    130                 135                 140

Leu Thr Gly Ala Lys Lys Ala Thr Ile His Thr Tyr Leu Ala Thr Ser
145                 150                 155                 160

Asp Met Phe Arg Glu Ile Val Phe Asn Met Ser Arg Glu Glu Ala Ile
                165                 170                 175

Ser Lys Ala Val Glu Ala Thr Lys Leu Val Arg Lys Leu Thr Lys Asp
            180                 185                 190

Asp Pro Ser Gln Gln Ala Thr Arg Trp Ser Tyr Glu Phe Ser Pro Glu
        195                 200                 205

Cys Phe Ser Asp Thr Pro Gly Glu Phe Ala Val Glu Ile Cys Glu Ala
    210                 215                 220

Val Lys Lys Ala Trp Glu Pro Thr Glu Glu Asn Pro Ile Ile Phe Asn
225                 230                 235                 240

Leu Pro Ala Thr Val Glu Val Ala Ser Pro Asn Val Tyr Ala Asp Gln
                245                 250                 255

Ile Glu Tyr Phe Ala Thr His Ile Thr Glu Arg Glu Lys Val Cys Ile
            260                 265                 270

Ser Thr His Cys His Asn Asp Arg Gly Cys Gly Val Ala Ala Thr Glu
        275                 280                 285

Leu Gly Met Leu Ala Gly Ala Asp Arg Val Glu Gly Cys Leu Phe Gly
    290                 295                 300

Asn Gly Glu Arg Thr Gly Asn Val Asp Leu Val Thr Val Ala Met Asn
305                 310                 315                 320

Met Tyr Thr Gln Gly Val Ser Pro Asn Leu Asp Phe Ser Asp Leu Thr
                325                 330                 335

Ser Val Leu Asp Val Val Glu Arg Cys Asn Lys Ile Pro Val Ser Gln
            340                 345                 350

Arg Ala Pro Tyr Gly Gly Asp Leu Val Val Cys Ala Phe Ser Gly Ser
        355                 360                 365

His Gln Asp Ala Ile Lys Lys Gly Phe Asn Leu Gln Asn Lys Lys Arg
    370                 375                 380

Ala Gln Gly Glu Thr Gln Trp Arg Ile Pro Tyr Leu Pro Leu Asp Pro
385                 390                 395                 400
```

-continued

```
Lys Asp Ile Gly Arg Asp Tyr Glu Ala Val Ile Arg Val Asn Ser Gln
                405                 410                 415

Ser Gly Lys Gly Gly Ala Ala Trp Val Ile Leu Arg Ser Leu Gly Leu
            420                 425                 430

Asp Leu Pro Arg Asn Met Gln Ile Glu Phe Ser Ser Ala Val Gln Asp
        435                 440                 445

His Ala Asp Ser Leu Gly Arg Glu Leu Lys Ser Asp Glu Ile Ser Lys
    450                 455                 460

Leu Phe Lys Glu Ala Tyr Asn Tyr Asn Asp Glu Gln Tyr Gln Ala Ile
465                 470                 475                 480

Ser Leu Val Asn Tyr Asn Val Glu Lys Phe Gly Thr Glu Arg Arg Val
                485                 490                 495

Phe Thr Gly Gln Val Lys Val Gly Asp Gln Ile Val Asp Ile Glu Gly
            500                 505                 510

Thr Gly Asn Gly Pro Ile Ser Ser Leu Val Asp Ala Leu Ser Asn Leu
        515                 520                 525

Leu Asn Val Arg Phe Ala Val Ala Asn Tyr Thr Glu His Ser Leu Gly
    530                 535                 540

Ser Gly Ser Ser Thr Gln Ala Ala Ser Tyr Ile His Leu Ser Tyr Arg
545                 550                 555                 560

Arg Asn Ala Asp Asn Glu Lys Ala Tyr Lys Trp Gly Val Gly Val Ser
                565                 570                 575

Glu Asp Val Gly Asp Ser Ser Val Arg Ala Ile Phe Ala Thr Ile Asn
            580                 585                 590

Asn Ile Ile His Ser Gly Asp Val Ser Ile Pro Ser Leu Ala Glu Val
        595                 600                 605

Glu Gly Lys Asn Ala Ala Ala Ser Gly Ser Ala
    610                 615

<210> SEQ ID NO 2
<211> LENGTH: 410
<212> TYPE: PRT
<213> ORGANISM: artificial sequence
<220> FEATURE:
<223> OTHER INFORMATION: synthetic polypeptide

<400> SEQUENCE: 2

Met Val Lys Glu Ser Ile Ile Ala Leu Ala Glu His Ala Ala Ser Arg
1               5                   10                  15

Ala Ser Arg Val Ile Pro Pro Val Lys Leu Ala Tyr Lys Asn Met Leu
                20                  25                  30

Lys Asp Pro Ser Ser Lys Tyr Lys Pro Phe Asn Ala Pro Lys Leu Ser
            35                  40                  45

Asn Arg Lys Trp Pro Asp Asn Arg Ile Thr Arg Ala Pro Arg Trp Leu
        50                  55                  60

Ser Thr Asp Leu Arg Asp Gly Asn Gln Ser Leu Pro Asp Pro Met Ser
65                  70                  75                  80

Val Glu Gln Lys Lys Glu Tyr Phe His Lys Leu Val Asn Ile Gly Phe
                85                  90                  95

Lys Glu Ile Glu Val Ser Phe Pro Ser Ala Ser Gln Thr Asp Phe Asp
            100                 105                 110

Phe Thr Arg Tyr Ala Val Glu Asn Ala Pro Asp Asp Val Ser Ile Gln
        115                 120                 125

Cys Leu Val Gln Ser Arg Glu His Leu Ile Lys Arg Thr Val Glu Ala
    130                 135                 140
```

Leu Thr Gly Ala Lys Lys Ala Thr Ile His Thr Tyr Leu Ala Thr Ser
145                 150                 155                 160

Asp Met Phe Arg Glu Ile Val Phe Asn Met Ser Arg Glu Glu Ala Ile
            165                 170                 175

Ser Lys Ala Val Glu Ala Thr Lys Leu Val Arg Lys Leu Thr Lys Asp
            180                 185                 190

Asp Pro Ser Gln Gln Ala Thr Arg Trp Ser Tyr Glu Phe Ser Pro Glu
            195                 200                 205

Cys Phe Ser Asp Thr Pro Gly Glu Phe Ala Val Glu Ile Cys Glu Ala
            210                 215                 220

Val Lys Lys Ala Trp Glu Pro Thr Glu Asn Pro Ile Ile Phe Asn
225                 230                 235                 240

Leu Pro Ala Thr Val Glu Val Ala Ser Pro Asn Val Tyr Ala Asp Gln
                245                 250                 255

Ile Glu Tyr Phe Ala Thr His Ile Thr Glu Arg Glu Lys Val Cys Ile
                260                 265                 270

Ser Thr His Cys His Asn Asp Arg Gly Cys Gly Val Ala Ala Thr Glu
            275                 280                 285

Leu Gly Met Leu Ala Gly Ala Asp Arg Val Glu Gly Cys Leu Phe Gly
            290                 295                 300

Asn Gly Glu Arg Thr Gly Asn Val Asp Leu Val Thr Val Ala Met Asn
305                 310                 315                 320

Met Tyr Thr Gln Gly Val Ser Pro Asn Leu Asp Phe Ser Asp Leu Thr
                325                 330                 335

Ser Val Leu Asp Val Val Glu Arg Cys Asn Lys Ile Pro Val Ser Gln
                340                 345                 350

Arg Ala Pro Tyr Gly Gly Asp Leu Val Val Cys Ala Phe Ser Gly Ser
            355                 360                 365

His Gln Asp Ala Ile Lys Lys Gly Phe Asn Leu Gln Asn Lys Lys Arg
            370                 375                 380

Ala Gln Gly Glu Thr Gln Trp Arg Ile Pro Tyr Leu Pro Leu Asp Pro
385                 390                 395                 400

Lys Asp Ile Gly Arg Asp Tyr Glu Ala Val
                405                 410

<210> SEQ ID NO 3
<211> LENGTH: 423
<212> TYPE: PRT
<213> ORGANISM: artificial sequence
<220> FEATURE:
<223> OTHER INFORMATION: synthetic polypeptide

<400> SEQUENCE: 3

Met Val Lys Glu Ser Ile Ile Ala Leu Ala Glu His Ala Ala Ser Arg
1               5                   10                  15

Ala Ser Arg Val Ile Pro Pro Val Lys Leu Ala Tyr Lys Asn Met Leu
                20                  25                  30

Lys Asp Pro Ser Ser Lys Tyr Lys Pro Phe Asn Ala Pro Lys Leu Ser
            35                  40                  45

Asn Arg Lys Trp Pro Asp Asn Arg Ile Thr Arg Ala Pro Arg Trp Leu
        50                  55                  60

Ser Thr Asp Leu Arg Asp Gly Asn Gln Ser Leu Pro Asp Pro Met Ser
65                  70                  75                  80

Val Glu Gln Lys Lys Glu Tyr Phe His Lys Leu Val Asn Ile Gly Phe
                85                  90                  95

```
Lys Glu Ile Glu Val Ser Phe Pro Ser Ala Ser Gln Thr Asp Phe Asp
                100                 105                 110

Phe Thr Arg Tyr Ala Val Glu Asn Ala Pro Asp Asp Val Ser Ile Gln
            115                 120                 125

Cys Leu Val Gln Ser Arg Glu His Leu Ile Lys Arg Thr Val Glu Ala
        130                 135                 140

Leu Thr Gly Ala Lys Lys Ala Thr Ile His Thr Tyr Leu Ala Thr Ser
145                 150                 155                 160

Asp Met Phe Arg Glu Ile Val Phe Asn Met Ser Arg Glu Glu Ala Ile
                165                 170                 175

Ser Lys Ala Val Glu Ala Thr Lys Leu Val Arg Lys Leu Thr Lys Asp
            180                 185                 190

Asp Pro Ser Gln Gln Ala Thr Arg Trp Ser Tyr Glu Phe Ser Pro Glu
        195                 200                 205

Cys Phe Ser Asp Thr Pro Gly Glu Phe Ala Val Glu Ile Cys Glu Ala
        210                 215                 220

Val Lys Lys Ala Trp Glu Pro Thr Glu Glu Asn Pro Ile Ile Phe Asn
225                 230                 235                 240

Leu Pro Ala Thr Val Glu Val Ala Ser Pro Asn Val Tyr Ala Asp Gln
                245                 250                 255

Ile Glu Tyr Phe Ala Thr His Ile Thr Glu Arg Glu Lys Val Cys Ile
                260                 265                 270

Ser Thr His Cys His Asn Asp Arg Gly Cys Gly Val Ala Ala Thr Glu
            275                 280                 285

Leu Gly Met Leu Ala Gly Ala Asp Arg Val Glu Gly Cys Leu Phe Gly
        290                 295                 300

Asn Gly Glu Arg Thr Gly Asn Val Asp Leu Val Thr Val Ala Met Asn
305                 310                 315                 320

Met Tyr Thr Gln Gly Val Ser Pro Asn Leu Asp Phe Ser Asp Leu Thr
                325                 330                 335

Ser Val Leu Asp Val Val Glu Arg Cys Asn Lys Ile Pro Val Ser Gln
            340                 345                 350

Arg Ala Pro Tyr Gly Gly Asp Leu Val Val Cys Ala Phe Ser Gly Ser
        355                 360                 365

His Gln Asp Ala Ile Lys Lys Gly Phe Asn Leu Gln Asn Lys Lys Arg
        370                 375                 380

Ala Gln Gly Glu Thr Gln Trp Arg Ile Pro Tyr Leu Pro Leu Asp Pro
385                 390                 395                 400

Lys Asp Ile Gly Arg Asp Tyr Glu Ala Val Ile Arg Val Asn Ser Gln
                405                 410                 415

Ser Gly Lys Gly Gly Ala Ala
                420
```

METABOLIC FLUX BIOSENSOR

CROSS-REFERENCE TO RELATED APPLICATIONS

This application is a national stage filing under 35 U.S.C. § 371 of International Application No. PCT/US2015/010665, filed Jan. 8, 2015, which was published under PCT Article 21(2) in English, and which claims the benefit under 35 U.S.C. § 119(e) of U.S. provisional application number 61/925,176, filed Jan. 8, 2014, each of which is incorporated by reference herein in its entirety.

FEDERALLY SPONSORED RESEARCH

This invention was made with government support under Grant No. 1F32GM098022-01A1 awarded by the National Institutes of Health. The government has certain rights in the invention.

BACKGROUND OF INVENTION

Fermentation technology is an essential component of the chemical and pharmaceutical industry. Microbes are used to produce many chemicals, fuels, and pharmacological agents including antibiotics, anticancer agents, cholesterol-lowering statins and immunosuppressants; and play an increasingly important role in the production of biopharmaceuticals such as hormones, vaccines and antibodies. Microorganisms are often used to synthesize drugs directly, but they can also be used to produce their chemical precursors in semi synthetic processes. A key advantage of biological production routes is the product stereo-specificity conferred by microorganisms, which enables the cost-effective production of drugs that would be otherwise economically unfeasible by purely chemical synthesis. The development of metabolic engineering has enabled the improvement of existing industrial fermentations, as well as the production of new drugs, chemicals and fuels.

SUMMARY OF INVENTION

Aspects of the present disclosure relate to the recognition that metabolic engineering is hindered by the lack of high throughput screen technologies, which can be used to identify factors (e.g., mutations in metabolic genes, small compounds, metabolites, etc.), which increase the production of metabolites or end products of metabolic pathways in microbes. For example, there is no convenient microbiological readout for factors that affect the microbial production of heavy alcohols, which are valuable for use in the pharmaceutical, food, chemical, and biofuels industries. Accordingly, provided herein are compositions and related methods useful for, inter alia, identifying factors which increase the production of metabolites and/or end products of metabolic pathways. Also provided are compositions and related methods useful for the production of metabolites and/or end products of metabolic pathways.

According to one aspect of the invention, cells are provided that include a recombinant nucleic acid construct comprising a promoter operably linked to a selectable marker, wherein the promoter is regulated by a nuclear receptor-like transcription factor, the activity of which is regulated by a small-molecule regulator; and wherein the cell expresses or is engineered to express the nuclear receptor-like transcription factor, which regulates the selectable marker depending on the presence or level of the small-molecule regulator. In certain embodiments, the cell is engineered to express the nuclear receptor-like transcription factor from a recombinant nucleic acid construct.

In some embodiments, the nuclear receptor-like transcription factor is a zinc cluster transcription factor or a Zn2Cys6 binuclear cluster transcription factor.

In some embodiments, the cell is engineered to reduce feedback inhibition of an enzyme that produces the small-molecule regulator, optionally wherein the enzyme is encoded by a recombinant nucleic acid construct. In certain embodiments, the feedback inhibition is reduced by mutating the enzyme that produces the small-molecule regulator, which mutation may, in some embodiments, be a point mutation or a deletion. In further embodiments, the wild-type enzyme that produces the small-molecule regulator is deleted or mutated.

In some embodiments, the small-molecule regulator is alpha-isopropylmalate and the enzyme that produces the small-molecule regulator is LEU4. In such embodiments, exemplary mutations of LEU4 of the yeast *Saccharomyces cerevisiae* include: a mutation or deletion of amino acid Ser547, a deletion of amino acids 411-619, a deletion of amino acids 424-619, a mutation of Gly514 or Gly516 to aspartic acid, a mutation of Ala552 to threonine, a mutation of Glu540 to lysine, a mutation of His541 to proline, a mutation of Ser519 to threonine, and a mutation of Asp578 to tyrosine.

In some embodiments, the nuclear receptor-like transcription factor is LEU3. In other embodiments, the nuclear receptor-like transcription factor is PUT3, GAL4/3, PPR1, LYS14, ARG81, WAR1, BAS1, PDR1, PDR3, OAF1, PIP2, HAP1, MAL63, RGT1, UPC2, ECM22, ARGRII, CHA4 or ARO80.

In some embodiments, the nuclear receptor-like transcription factor is a transcription factor engineered to respond to a different small-molecule regulator than the corresponding wild-type, unmodified, nuclear receptor-like transcription factor responds to.

In some embodiments, the small-molecule regulator is an intracellular metabolite, such as an intermediate in the pathway regulated by the nuclear receptor-like transcription factor.

In some embodiments, the cell also includes a gene product that synthesizes the small-molecule regulator or a gene product that is upstream of the gene product that synthesizes the small-molecule regulator in a pathway. In certain embodiments, the gene product that synthesizes the small-molecule regulator is an enzyme that produces the small-molecule regulator.

In some embodiments, the nuclear receptor-like transcription factor is LEU3 and the small-molecule regulator is alpha-isopropylmalate.

In some embodiments, the promoter is a promoter regulated in vivo by the nuclear receptor-like transcription factor. In certain of these embodiments, the nuclear receptor-like transcription factor is LEU3 and the promoter is LEU1, ILV2, LEU4, BAP2, BAT2 or GDH1. In some embodiments, the promoter is a *S. cerevisiae* promoter.

In other embodiments, the promoter is an engineered synthetic promoter. In some of these embodiments, the engineered synthetic promoter binds two or more of the nuclear receptor-like transcription factors or dimers of the nuclear receptor-like transcription factors.

In some embodiments, the selectable marker is a reporter gene. In certain embodiments, the reporter gene encodes a fluorescent protein or a luminescent protein, such as a green fluorescent protein (e.g., GFP, EGFP, Clover, Emerald, GFPγ, MaxGFP, Superfolder GFP, mWasabi), a red fluorescent protein (e.g., RFP, mCherry, mRuby, mRuby2, mApple, mKate2, mKO2, or TagRFP-T), a yellow fluorescent protein (e.g., YFP), or a blue fluorescent protein (e.g., BFP, mTagBFP, mTagBFP2), or a luciferase (e.g., firefly, Renilla, Gaussia). In some embodiments, a tag that modified protein stability, such as a PEST sequence, is added to the fluorescent protein or the luminescent protein.

In some embodiments, the nucleic acid construct comprises the coding sequence of the selectable marker fused to the coding sequence of the native gene regulated by the promoter.

In some embodiments, the selectable marker is an auxotrophic marker, such as URA3, HIS3, ADE1, ADE2, LEU2, LYS2, or TRP1 or MET15.

In other embodiments, the selectable marker is a gene that confers temperature sensitivity, reduced temperature sensitivity in a temperature sensitive strain, colony color, colony morphology, resistance to an antibiotic, resistance to a toxin or resistance to a toxic condition.

In some embodiments, the cell is a fungal cell, such as a yeast cell, for example a Saccharomyces cerevisiae cell, a bacterial cell, an archaeal cell, and/or a plant cell.

In some embodiments, the cell is engineered or selected to produce or have altered, optionally increased, production of a molecule of interest. In certain of these embodiments, the cell overexpresses one or more genes in a metabolic pathway. In other of these embodiments, the cell expresses one or more genes from a different organism, optionally a gene involved in the synthesis of the molecule of interest. In other of these embodiments, the cell comprises a deletion or mutation of one or more genes, optionally wherein the one or more genes that are deleted or mutated are in a competing metabolic pathway. In other of these embodiments, the cell has altered transport of one or more molecules, such as increased uptake of a precursor of the molecule of interest, decreased export of the molecule of interest, or increased export of the molecule of interest. In other of these embodiments, the cell is selected or engineered to be resistant to high levels of the molecule of interest or intermediates in or byproducts of synthesis of the molecule of interest.

In some embodiments, the cell includes one or more recombinant nucleic acid constructs collectively comprising at least two promoters, each promoter operably linked to a different selectable marker, wherein the promoters are regulated by different nuclear receptor-like transcription factors, the activity of each of which is regulated by a different small-molecule regulator.

In some embodiments, the cell includes one or more recombinant nucleic acid constructs collectively comprising at least two promoters, each promoter operably linked to a different selectable marker, wherein the promoters are regulated by the same nuclear receptor-like transcription factor, with the different promoters having different sensitivity and/or dynamic range in their response to activation by the receptor-like transcription factor, the activity of which is regulated by the same small molecule regulator.

In some embodiments, the one or more recombinant nucleic acid constructs (i) is/are integrated into the genome; (ii) is one or more low copy number vectors; or (iii) is one or more high copy number vectors.

According to another aspect of the invention, compositions are provided that include any of the foregoing cells. In some embodiments, the composition also includes a factor to be tested. In some embodiments, the factor is one or more types of small organic molecule.

In some embodiments, the factor is one or more genes or gene products that is/are added to the cell, mutated in the cell, overexpressed in the cell, reduced in expression or activity in the cell or deleted from the cell. In some embodiments, the factor is one or more molecules that regulate one or more genes or gene products, such as a CRISPR-based system for changing gene regulation, including for interference, inhibition, or activation of gene expression. In some embodiments, the one or more genes or gene products is in a pathway that includes the small-molecule regulator that regulates the nuclear receptor-like transcription factor. In some embodiments, the one or more genes or gene products is a nucleic acid or library of nucleic acids that inhibit or activate proteins or that encodes polypeptides that inhibit or activate proteins, such as recombinant single domain antibodies, optionally camelid single domain antibodies.

According to another aspect of the invention, methods of making the foregoing cells are provided. The methods include introducing into a cell a nucleic acid construct comprising a promoter operably linked to a selectable marker, wherein the promoter is regulated by a nuclear receptor-like transcription factor, the activity of which is regulated by a small-molecule regulator, and wherein the cell expresses the nuclear receptor-like transcription factor, which regulates the selectable marker depending on the presence or level of the small-molecule regulator.

In some embodiments, the methods also include engineering the cell to reduce feedback inhibition of an enzyme that produces the small-molecule regulator.

According to another aspect of the invention, nucleic acid constructs are provided. The nucleic acid constructs include sequences coding for at least two of (1) a promoter operably linked to a selectable marker, wherein the promoter is regulated by a nuclear receptor-like transcription factor, the activity of which is regulated by a small-molecule regulator; (2) a nuclear receptor-like transcription factor that binds to and regulates transcription by the promoter; and (3) a gene product that synthesizes the small-molecule regulator or a gene product that is upstream in a pathway of the gene product that synthesizes the small-molecule regulator. The promoter, selectable marker, nuclear receptor-like transcription factor and gene product that synthesizes the small-molecule regulator (or is upstream) are optionally as described above in connection with the cells. In some embodiments, the nucleic acid construct is a vector, optionally a plasmid. In certain embodiments, the plasmid is a high copy number plasmid or a low copy number plasmid.

In some embodiments, the promoter in the nucleic acid construct comprises one or more UASs for LEU3. In certain embodiments, the promoter is a LEU1, ILV2, LEU4, BAP2, BAT2 or GDH1 promoter. In some embodiments, the promoter is a S. cerevisiae promoter.

In some embodiments, the nuclear receptor-like transcription factor in the nucleic acid construct is LEU3.

In some embodiments, the gene product that synthesizes the small-molecule regulator nucleic acid construct is LEU4. In certain embodiments, the LEU4 is a leucine-insensitive LEU4 mutant.

According to another aspect of the invention, methods for screening for factors that affect metabolic pathways are provided. The methods include: 1) (a) providing any of the foregoing cells or a composition including such cells, and introducing a factor to be screened into the cell or contacting the cell with a factor to be screened, or (b) providing a composition including any of the foregoing cells and a factor to be tested; and 2) detecting a gene product of the selectable marker. An increase or decrease of the gene product of the selectable marker indicates that the factor is one that affects a metabolic pathway. In some embodiments, introducing a factor to be screened into the cell includes mutagenizing one or more endogenous gene(s) of the cell, such as by with UV or chemical mutagenesis. The selectable marker can be detected by detecting a gene product of the selectable marker or by detecting a result of the expression of the selectable marker.

In some embodiments, the factor is one or more types of small organic molecule.

In other embodiments, the factor is one or more genes or gene products that is/are added to the cell, mutated in the cell, overexpressed or activated in the cell, reduced in expression or activity in the cell or deleted from the cell.

In some embodiments, the factor is one or more molecules that regulate one or more genes or gene products, such as a CRISPR-based system for changing gene regulation.

In some embodiments, the one or more genes or gene products is in a pathway that includes the small-molecule regulator that regulates the nuclear receptor-like transcription factor. In other embodiments, the one or more genes or gene products is a nucleic acid or library of nucleic acids that inhibit or activate proteins or that encodes polypeptides that inhibit or activate proteins, such as recombinant single domain antibodies, optionally camelid single domain antibodies.

In some embodiments, if the factor is a gene or gene product mutated in the cell or added to the cell, then the method further includes isolating at least a portion of the gene, optionally sequencing at least the portion of the gene, and/or optionally introducing the mutated or added gene into a different cell.

In some embodiments, the factor identified as one that affects a metabolic pathway is a factor that increases synthesis or reduces degradation of a molecule that is a product, an intermediate or a side product of the metabolic pathway. In certain embodiments, the factor identified as one that affects a metabolic pathway is a factor that increases synthesis of a molecule that is a product of the metabolic pathway. In certain embodiments, the factor identified as one that affects a metabolic pathway is a factor that results in increased levels of a molecule that is a product of the metabolic pathway.

In other embodiments, the factor identified as one that affects a metabolic pathway is a factor that reduces synthesis or increases degradation of a molecule that is a product, an intermediate or a side product of the metabolic pathway.

In other embodiments, the factor identified as one that affects a metabolic pathway is a factor that increases or decreases export of a molecule from the cell that is a product, an intermediate or a side product of the metabolic pathway.

In other embodiments, the factor identified as one that affects a metabolic pathway is a factor that improves or alters substrate utilization, or allows use of one or more different substrate(s).

In some embodiments, the methods also include detecting, measuring or isolating the molecule that is a product, an intermediate or a side product of the metabolic pathway.

In some embodiments, the small-molecule regulator that regulates the nuclear receptor-like transcription factor in the cell is a proxy for synthesis of a different molecule. In certain of these embodiments, the small-molecule regulator is alpha-isopropylmalate, which is a proxy for synthesis of branched-chain amino acids and for alcohol production.

In some embodiments, an increase of the gene product of the selectable marker indicates that the factor increases synthesis of a molecule of interest produced by the pathway and/or increases flux through the pathway.

According to another aspect of the invention, methods for producing a molecule produced by a metabolic pathway are provided. The methods include providing a cell that comprises a factor identified in any of the foregoing methods or that is contacted with a factor identified in any of any of the foregoing methods, and culturing the cell under suitable conditions for a time sufficient to produce the molecule. In some embodiments, the methods further include isolating the molecule from the cells, from the culture, or from medium in which the cell is or was cultured.

According to another aspect of the invention, methods are provided for screening for cells that have a selected metabolic pathway or that have an alteration in a selected metabolic pathway, such as an alteration that results in increased synthesis or level of a molecule of interest. The methods include 1) (a) providing a cell, and introducing into the cell any of the foregoing recombinant nucleic acid constructs, wherein the promoter operably linked to the selectable marker is regulated by a nuclear receptor-like transcription factor that is in the selected metabolic pathway or a nuclear receptor-like transcription factor that is regulated by a small-molecule regulator of the selected metabolic pathway, or (b) providing a cell that includes any of the foregoing recombinant nucleic acid constructs; and 2) detecting a gene product of the selectable marker. The gene product of selectable marker indicates that the cell is one that has the selected metabolic pathway. The selectable marker can be detected, for example, by detecting a gene product of the selectable marker or by detecting a result of the expression of the selectable marker.

According to another aspect of the invention, methods for producing a molecule produced by a metabolic pathway are provided. The methods include providing a cell identified by the foregoing method for screening for cells that have a selected metabolic pathway, and culturing the cell under suitable conditions for a time sufficient to produce the molecule. In some embodiments, the methods further include isolating the molecule from the cells, from the culture, or from medium in which the cell is or was cultured.

In the foregoing compositions and methods, metabolites include small molecules, peptides, large proteins, lipids, sugars, etc. Exemplary metabolites include amino acids; alcohols including ethanol and heavy alcohols; and therapeutic proteins, such as antibodies or antibody fragments.

Other advantages, features, and uses of the invention will be apparent from the Detailed Description of the Invention; the Drawings; and the Claims.

BRIEF DESCRIPTION OF DRAWINGS

FIG. 3A presents activity of the biosensor Construct A by flow cytometry in the presence or absence of leucine. Fluorescence of yellow fluorescent protein (YFP) is shown. Left trace: negative control construct without fluorescent protein. Middle trace: leucine added to culture. Right trace: no leucine added to culture. FIG. 3B presents phase contrast micrographs (left panels) and corresponding fluorescence micrographs (right panels) of yeast cells comprising the ORF replacement biosensor Construct A in S. cerevisiae cultured in the presence (top panels) or absence of leucine (bottom panels). In the presence of leucine, the YFP reporter of the biosensor is not expressed, due to repression of YFP expression by Leu3 based on reduced levels of α-IPM via feedback inhibition of Leu4 (see FIG. 1). In the absence of leucine the biosensor is induced due to activation of YFP expression by Leu3 based on increased levels of α-IPM via activation of Leu4 due to reduced levels of leucine.

FIG. 4A and FIG. 4B show expression of the Leu3-regulated biosensor Construct B in S. cerevisiae. FIG. 4A shows phase contrast micrographs (left panels) and corresponding fluorescence micrographs (right panels) of yeast cells comprising the biosensor Construct B cultured in the presence (top panels) or absence of leucine (bottom panels). FIG. 4B shows activity of the biosensor in the presence or absence of leucine by flow cytometry. Fluorescence of green fluorescent protein (GFP) is shown. Left trace: negative control construct without GFP. Middle trace: leucine added to culture. Right trace: no leucine added to culture. In the presence of leucine, the GFP reporter of the biosensor is not expressed, due to repression of GFP expression by Leu3 based on reduced levels of α-IPM via feedback inhibition of Leu4 (see FIG. 1). In the absence of leucine, the biosensor is induced due to activation of GFP expression by Leu3 based on increased levels of α-IPM via activation of Leu4 due to reduced levels of leucine.

FIG. 5A presents activity of the biosensor by flow cytometry in S. cerevisiae strains encoding wild-type Leu4 protein or a leucine-insensitive mutant Leu4 protein (ΔS547) in the presence or absence of leucine. Fluorescence of green fluorescent protein (GFP) is shown. Left thick trace: negative control construct without GFP. Middle thick trace: Leu4 ΔS547 expressed with leucine added to culture. Right thick trace: Leu4 ΔS547 expressed with no leucine added to culture. Left thin trace: wild-type Leu4 expressed with leucine added to culture. Right thin trace: wild-type Leu4 expressed with no leucine added to culture. FIG. 5B presents a ribbon structure of the mutant Leu4 protein indicating the location of the S547 deletion.

FIG. 6A presents activity of the biosensor by flow cytometry in S. cerevisiae strains encoding wildtype Leu4 or a Leu4 protein lacking the regulatory domain in the presence or absence of leucine. Fluorescence of green fluorescent protein (GFP) is shown. Left thick trace: negative control construct without GFP. Middle thick trace: truncated Leu4 expressed with leucine added to culture. Right thick trace: truncated Leu4 expressed with no leucine added to culture. Left thin trace: wild-type Leu4 expressed with leucine added to culture. Right thin trace: wild-type Leu4 expressed with no leucine added to culture. FIG. 6B presents a ribbon structure of the truncated Leu4 protein lacking the β-sandwich regulatory domain.

FIGS. 7A-7D show activity of the biosensor Construct A in S. cerevisiae in the presence of various concentrations of α-IPM. FIG. 7A shows fluorescence (top panel) and phase contrast (bottom panel) micrographs of cells in the absence of leucine. FIG. 7B shows fluorescence (left panel) and phase contrast (right panel) micrographs of cells in the presence of leucine. FIG. 7C shows fluorescence (left panel) and phase contrast (right panel) micrographs of cells in the presence of leucine and 20 mM α-IPM. FIG. 7D shows fluorescence (left panel) and phase contrast (right panel) micrographs of cells in the presence of leucine and 100 mM α-IPM.

FIG. 8A shows fluorescence (top panel) and phase contrast (bottom panel) micrographs of cells in the absence of leucine. FIG. 8B shows fluorescence (left panel) and phase contrast (right panel) micrographs of cells in the presence of leucine. FIG. 8C shows fluorescence (left panel) and phase contrast (right panel) micrographs of cells in the presence of leucine and 20 mM α-IPM. FIG. 8D shows fluorescence (left panel) and phase contrast (right panel) micrographs of cells in the presence of leucine and 100 mM α-IPM.

FIG. 9A shows fluorescence (top panel) and phase contrast (bottom panel) micrographs of cells in the absence of leucine. FIG. 9B shows fluorescence (left panel) and phase contrast (right panel) micrographs of cells in the presence of leucine. FIG. 9C shows fluorescence (left panel) and phase contrast (right panel) micrographs of cells in the presence of leucine and 20 mM α-IPM. FIG. 9D shows fluorescence (left panel) and phase contrast (right panel) micrographs of cells in the presence of leucine and 100 mM α-IPM.

FIG. 10A shows activity of the biosensor Construct A in S. cerevisiae. FIG. 10B shows activity of the biosensor Construct B in S. cerevisiae over-expressing Leu3. FIG. 10C shows activity of the biosensor Construct A in S. cerevisiae over-expressing Leu3. Fluorescence of YFP or GFP is shown. Left thin trace: negative control construct without fluorescent protein. Middle thin trace: no α-IPM added to culture. Right thin trace: no α-IPM or leucine added to culture. Left thin trace: wild-type Leu4 expressed with leucine added to culture. Right trace: wild-type Leu4 expressed with no leucine added to culture. Thick traces: left to right, 2 mM, 20 mM, 50 mM or 100 mM α-IPM added to culture.

FIGS. 11A and 11B show S. cerevisiae colonies comprising the metabolic flux biosensor cultured on solid medium allowing for selection of colonies with enhanced leucine biosynthesis. FIG. 11A shows colonies on solid medium and FIG. 11B shows a fluorescence scan of the same solid medium plate. The presence and intensity of fluorescence of the colonies in FIG. 11B indicates that the level expression of the biosensor serves as a proxy for the leucine biosynthetic pathway in the cells comprising the colony.

FIG. 12A shows flow cytometry analysis of S. cerevisiae in which the two types of cells are identified based on the level of expression of the biosensor (GFP as reporter). The gate indicates the population with higher fluorescence that was collected. FIG. 12B shows samples from a S. cerevisiae culture before and after enrichment based on cell sorting. Colonies that form on the replica plating on YPD+kanamycin medium express the biosensor as shown by kanamycin-resistance.

FIG. 13A shows flow cytometry analysis S. cerevisiae in which the gate indicates the population with highest biosensor expression (<1% of total cells) that was collected. FIG. 13B shows samples from the S. cerevisiae culture before and after enrichment based on cell sorting. Colonies that form on the replica plating on YPD+kanamycin medium express the biosensor as shown by kanamycin-resistance.

FIG. 14 presents exemplary activators and metabolite inducer molecules that can be used to design metabolic flux biosensors to indirectly assess production of desired products including products of the pathways of the activators See Sellick and Reece, Trends Biochem Sci. 2005 July; 30(7): 405-12 for structures of the indicated metabolic activators.

FIG. 19A shows response to α-IPM of a biosensor Construct A (squares) and biosensor Construct B (circles). FIG. 19B shows response to α-KIV of a biosensor Construct A (squares) and biosensor Construct B (circles). FIG. 19C shows response to α-KIV of biosensor Construct B in yeast cells expressing wild-type LEU4 (circles) and biosensor Construct B in LEU4 mutant yeast cells (leucine-independent LEU4, triangles). The reported values are the mean fluorescence of 100,000 cells counted in a Fortessa flow cytometer, reported in arbitrary units of fluorescence (AUF).

FIG. 20A shows fluorescence signal from biosensor Construct A (FIG. 20A). FIG. 20B shows fluorescence signal from biosensor Construct B. Squares correspond to biosensors in yeast expressing wild-type LEU4, and circles correspond to biosensors in LEU4 mutant yeast cells (leucine-independent LEU4).

FIG. 21A shows a flow cytometry histogram of yeast containing a Construct B Leu3 biosensor, transformed with a pooled library of the 2μ overexpression collection (dark gray histogram), compared to the histogram of the same strain transformed with empty plasmid (overlaid light gray histogram). The remaining population from the cells transformed with the overexpression collection that fall outside the boundary of the range of the histogram of cells transformed with an empty plasmid are potentially enriched with genes that cause hypo- or hyper activation of the BCA pathway. FIG. 21B shows flow cytometry histograms for an isolated mutant that has a hyperactive BCA pathway that is still sensitive to leucine inhibition. FIG. 21C shows flow cytometry histograms for an isolated mutant that has a hyperactive BCA pathway insensitive to leucine.

DETAILED DESCRIPTION OF INVENTION

Figure 1:
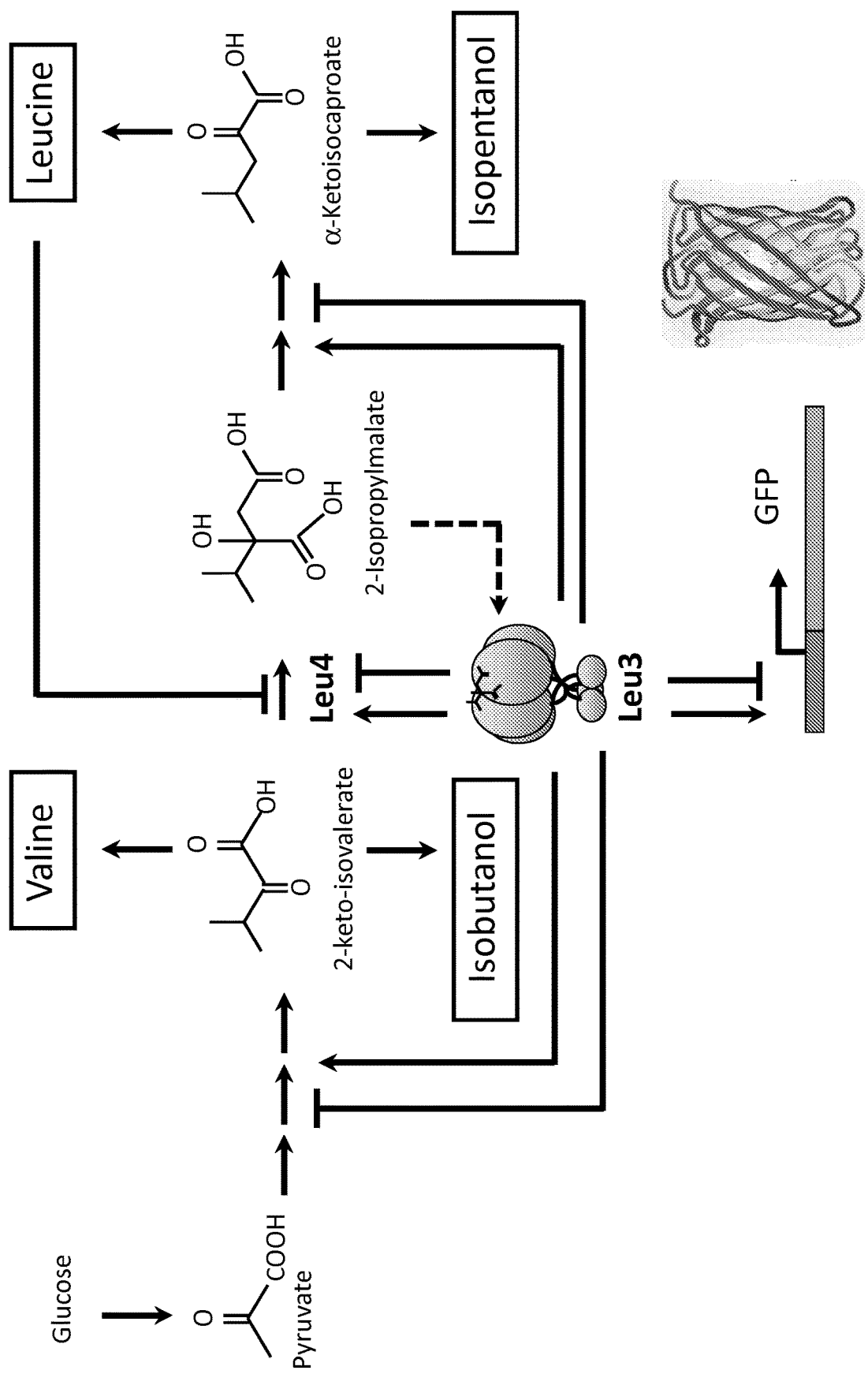
FIG. 1 shows a schematic representation of the leucine biosynthetic pathway and an exemplary metabolic flux biosensor based on the regulation of the leucine biosynthetic pathway. The leucine biosynthetic pathway is regulated by end-product inhibition. In the absence of leucine, α-isopropylmalate (α-IPM) is produced by Leu4 and binds to the transcription factor, Leu3. α-IPM-bound Leu3 is able to bind promoters to activate genes in the leucine biosynthetic pathway. The metabolic flux biosensor couples a Leu3-regulatable promoter to a selectable marker (e.g. reporter gene encoding GFP) such that in the absence of leucine, the selectable marker is expressed. In the presence of leucine, Leu4 is inactivated and does not produce α-IPM. Leu3, when not bound to α-IPM, functions as a repressor of genes in the leucine biosynthetic pathway. In the exemplary metabolic flux biosensor depicted in this figure, Leu3 not bound to α-IPM functions as a repressor of a selectable marker (e.g. the reporter gene encoding GFP shown here).

Metabolic engineering is the practice of optimizing genetic and regulatory processes within cells to increase, create, or otherwise augment their ability to produce a desired substance. These processes are chemical networks that use a series of biochemical reactions and enzymes that allow cells to convert raw materials into molecules of interest. Genetic engineering techniques can be used to modify the networks in order to enhance or modify the production of certain molecules, and can also be used to establish such networks in cells that would otherwise lack the capacity to metabolize a given substance into a desired molecule. The ultimate goal of metabolic engineering is to use these modified organisms to produce valuable substances on an industrial scale in a cost effective manner. Current examples include producing beer, wine, cheese, pharmaceuticals, and other biotechnology products.

Since cells use these metabolic networks for their survival, changes can have drastic effects on cell viability. Therefore, trade-offs in metabolic engineering arise between the cells ability to produce the desired substance and its natural survival needs. For example, instead of directly deleting and/or overexpressing the genes that encode for metabolic enzymes, one approach is to target the regulatory networks in a cell to efficiently engineer a desired metabolism. However, current technologies for screening or identifying factors that favorably affect a particular metabolic pathway are inefficient, resulting in increased time and expense to identify engineered organisms of interest. For example, it may be desirable to increase the flux of a given metabolic pathway by increasing the production of a certain metabolic intermediate. However, there exists no efficient and facile means for screening, e.g., a library of mutations which may contain a single mutant that increases the production of an intermediate.

Accordingly, aspects of the present disclosure provide compositions and methods useful for identifying factors that favorably affect metabolic pathways, e.g., compositions and methods pertaining to high-throughput screening assays. Also provided, are compositions and methods useful for producing metabolites and end products, for example heavy alcohols (e.g., isobutanol, isopentanol).

In some embodiments, cells useful according to the methods described herein are provided. For example, in some embodiments cells are provided which are useful as metabolic flux biosensors, e.g., for use in high-throughput screening assays described herein. In some embodiments, a cell-based metabolic flux biosensor allows the in vivo monitoring and high-throughput screening of mutations (e.g., in a metabolic gene) or conditions (e.g., growth conditions, exogenously added small compounds or molecules, etc.) that affect mitochondrial physiology in favor of engineered heavy alcohol biosynthetic pathways. For example, in some embodiments cells are provided which have been engineered to provide a readout of metabolic flux through biosynthetic/metabolic pathways which can lead to heavy alcohol production, e.g., the Ehrlich pathway, the acetone-butanol-ethanol (ABE) pathway, and the branched chain amino acid (BCAA) pathway (e.g., via the branched chain α-keto acid dehydrogenase complex (BCKDC)).

In some embodiments, the cells comprise a nucleic acid construct comprising a promoter operably linked to a selectable marker. The promoter is typically one that it is regulated in vivo by transcription factor, e.g., a nuclear receptor-like transcription factor. In some embodiments, the activity of the nuclear receptor-like transcription factor is regulated by a small-molecule regulator. In some embodiments, "small-molecule regulator" refers to a ligand which regulates the expression of one or more metabolic genes. Examples of small-molecule regulators include, but are not limited to, small molecules including environmental chemicals, nutrients, and cellular metabolites. Typically, the small-molecule regulator regulates the activity of a transcription factor (e.g., a nuclear receptor-like transcription factor), through binding to the transcription factor or a co-factor that interacts with the transcription factor (e.g., a co-activator or co-repressor). For example and without being bound to any particular mechanism, in the absence of the small-molecule regulator being bound to the transcription factor (and/or co-factor), the transcription factor represses the promoter such that the selectable marker is not expressed. When the small-molecule regulator is present and bound to the transcription factor (and/or co-factor), the promoter is active and the selectable marker is expressed. Expression of the selectable marker is a readout of the presence of the small-molecule regulator in the cell, and in some embodiments, indicates metabolic flux.

In some embodiments, the transcription factor is a nuclear receptor-like transcription factor. Nuclear receptor-like transcription factors are known in the art, and include those described by Todd and Andrianopoulos, *Fungal Genet Biol.* 1997 June; 21(3):388-405; Sellick and Reece, *Trends Biochem Sci.* 2005 July; 30(7):405-12; Oba et al., *Biosci Biotechnol Biochem.* 2005 July; 69(7):1270-3; and Näär and Thakur, *Genes Dev.* 2009 Feb. 15; 23(4):419-32; the entire contents of each are hereby incorporated by reference. In some embodiments, the nuclear receptor-like transcription factor is a zinc cluster transcription factor and/or a Zn2Cys6 binuclear cluster transcription factor. In some embodiments, the terms "zinc cluster transcription factor" and "Zn2Cys6 binuclear cluster transcription factor" are used interchangeably. Zn2Cys6 binuclear cluster transcription factors are known in the art, and include those described by Todd and Andrianopoulos, *Fungal Genet Biol.* 1997; Rottensteiner et al., *Eur J Biochem.* 1997 Aug. 1; 247(3):776-83; Noel and Turcotte, *J Biol Chem.* 1998 Jul. 10; 273(28):17463-8; Iraqui et al., *Mol Cell Biol.* 1999 May; 19(5):3360-71; Nikolaev et al., *J Biol Chem.* 1999 Apr. 2; 274(14):9795-802; MacPherson et al., *Microbiol Mol Biol Rev.* 2006 September; 70(3): 583-604. Hong et al., *Structure.* 2008 July; 16(7):1019-26. Ehrlich et al., *Toxins (Basel).* 2012 December; 4(12):1582-1600; Sun et al., *Fungal Genet Biol.* 2012 May; 49(5):379-87; Bovier et al., *Eukaryot Cell.* 2014 January; 13(1):53-65; the entire contents of each are hereby incorporated by reference. In some embodiments, the nuclear receptor-like transcription factor is one or more selected from the following non-limiting list: LEU3, PUT3, GAL4/3, PPR1, LYS14, ARG81, WAR1, BAS1, PDR1, PDR3, OAF1, PIP2, HAP1, MAL63, RGT1, UPC2, ECM22, ARGRII, CHA4 and ARO80. In some embodiments, the nuclear receptor-like transcription factor is LEU3. In some embodiments, the nuclear receptor-like transcription factor is a transcription factor engineered to respond to a different small-molecule regulator than the corresponding wild-type, unmodified, nuclear receptor-like transcription factor responds to. For example, in some embodiments, the regulatory ligand binding domain of a transcription factor or co-factor (e.g., small-molecule regulator binding domain of a transcription factor or co-factor) can be cloned and fused to another transcription factor or co-factor, thereby altering is regulatory activity. Other methods for engineering transcription factors are known in the art, and include for example, those described by Peet et al., *Chem Biol.* 1998 January; 5(1):13-21; Beerli et al., *J Biol Chem.* 2000 Oct. 20; 275(42):32617-27; Chen and Zhao, *Mol Biol.* 2005 May 20; 348(5):1273-82; and Reetz et al., Methods in Enzymology. 2007 388: 91-102; the entire contents of each are hereby incorporated by reference.

In some embodiments, the small-molecule regulator is an intracellular metabolite, which can be, in some embodiments, an intermediate in the pathway regulated by the nuclear receptor-like transcription factor. In some embodiments, the intracellular metabolite is an intermediate in a metabolic pathway that can lead to the production of heavy alcohols, e.g., a metabolite in the Ehrlich pathway, the acetone-butanol-ethanol (ABE) pathway, and/or the branched chain amino acid (BCAA) pathway (e.g., via the branched chain α-keto acid dehydrogenase complex (BCKDC)). In some embodiments, the small-molecule regulator is alpha-isopropylmalate (α-IPM). In some embodiments, the nuclear receptor-like transcription factor is LEU3 and the small-molecule regulator is alpha-isopropylmalate.

In some embodiments, the cell further comprises a gene product that synthesizes the small-molecule regulator. In some embodiments, the cell comprises a gene product that is upstream of the gene product that synthesizes the small-molecule regulator in a pathway. For example, in some embodiments the gene product that synthesizes the small-molecule regulator is an enzyme that produces the small-molecule regulator. In some embodiments, the small-molecule regulator is not produced by the cell.

In some embodiments, the promoter is one that it is regulated by a nuclear receptor-like transcription factor, e.g., as described herein. For example, in some embodiments the promoter is derived from a metabolic gene. In some embodiments, the promoter is (is derived from) LEU1, ILV2, LEU4, BAP2, BAT2 or GDH1, which may be regulated by the nuclear receptor-like transcription factor LEU3. In some embodiments, the promoter is a *S. cerevisiae* promoter. In some embodiments, the promoter is an engineered synthetic promoter, for example a promoter engineered to bind one, two or more of the nuclear receptor-like transcription factors or dimers of the nuclear receptor-like transcription factors. Methods for engineering promoters are well-known, and include for example, those described by Blazeck and Alper, *Biotechnol J.* 2013 January; 8(1):46-58, the entire contents of which are incorporated by reference.

In some embodiments, the selectable marker is a reporter gene, for example a reporter gene encoding a fluorescent protein or a luminescent protein. Reporter genes encoding fluorescent or luminescent proteins are well known, and include, for example, green fluorescent proteins (e.g., GFP, EGFP, Clover, Emerald, GFPγ, MaxGFP, Superfolder GFP, mWasabi), red fluorescent proteins (e.g., RFP, mCherry, mRuby, mRuby2, mApple, mKate2, mKO2, or TagRFP-T), yellow fluorescent proteins (e.g., YFP), blue fluorescent proteins (e.g., BFP, mTagBFP, mTagBFP2), and luminescent proteins such as a luciferase (e.g., firefly, Renilla, Gaussia). In some embodiments, the reporter gene comprises a tag that modifies the stability of the reporter protein, such as a PEST sequence (e.g., a peptide sequence that is rich in proline (P), glutamic acid (E), serine (S), and threonine (T). PEST sequences are known in the art (Rogers and Rechsteiner, *Science*, 1986 234 (4774): 364-8), and provide a signal for targeted degradation of the reporter gene product, which in some embodiments, results in faster turn-over of the reporter which can reduce background and increase the dynamic range in certain screening assays described herein. In some embodiments, the selectable marker is an auxotrophic marker. In some embodiments, the auxotrophic marker is URA3, HIS3, ADE1, ADE2, LEU2, LYS2, TRP1 or MET15. In some embodiments, the selectable marker is a gene that confers temperature sensitivity, reduced temperature sensitivity in a temperature sensitive strain, colony color, colony morphology, resistance to an antibiotic, resistance to a toxin or resistance to a toxic condition.

In some embodiments, the cell is any cell capable of being metabolically engineered to produce a desired metabolite or end product of a metabolic pathway. In some embodiments, the cell is a eukaryotic or prokaryotic cell. In some embodiments, the cell is a prokaryotic cell such as those belonging to the genus *Clostridia* (e.g., *C. botulinum, C. tetani, C. perfrigens*, and *C. difficile*) or strains of *Escherichia coli* (e.g., as provided in Kim et al., *Biotechnol J.* 2013 Sep. 25). In some embodiments, the cell is a fungal cell. In some embodiments, the cell is a yeast cell, e.g., a *Saccharomyces cerevisiae* cell.

Thus cells useful in the invention include prokaryotic cells and eukaryotic cells. Prokaryotic cells include bacterial cells and archaeal cells. Eukaryotic cells include yeast cells, mammalian cells, plant cells, insect cells, stem cells, and fungus cells. Eukaryotic cells may be contained in, e.g., part of or all of, a multicellular organism. Multicellular organisms include mammals, nematodes such as *Caenorhabditis elegans*, plants such as *Arabidopsis thaliana, Bombyx mori, Xenopus laevis*, zebrafish (*Danio rerio*), sea urchin and *Drosophila melanogaster*.

Examples of bacteria include *Escherichia* spp., *Streptomyces* spp., *Zymonas* spp., *Acetobacter* spp., *Citrobacter* spp., *Synechocystis* spp., *Rhizobium* spp., *Clostridium* spp., *Corynebacterium* spp., *Streptococcus* spp., *Xanthomonas* spp., *Lactobacillus* spp., *Lactococcus* spp., *Bacillus* spp., *Alcaligenes* spp., *Pseudomonas* spp., *Aeromonas* spp., *Azotobacter* spp., *Comamonas* spp., *Mycobacterium* spp., *Rhodococcus* spp., *Gluconobacter* spp., *Ralstonia* spp., *Acidithiobacillus* spp., *Microlunatus* spp., *Geobacter* spp., *Geobacillus* spp., *Arthrobacter* spp., *Flavobacterium* spp., *Serratia* spp., *Saccharopolyspora* spp., *Thermus* spp., *Stenotrophomonas* spp., *Chromobacterium* spp., *Sinorhizobium* spp., *Saccharopolyspora* spp., *Agrobacterium* spp. and *Pantoea* spp.

Examples of archaea (also known as archaebacteria) include *Methylomonas* spp., *Sulfolobus* spp., *Methylobacterium* spp. *Halobacterium* spp., *Methanobacterium* spp., *Methanococci* spp., *Methanopyri* spp., *Archaeoglobus* spp., *Ferroglobus* spp., *Thermoplasmata* spp. and *Thermococci* spp.

Examples of yeast include *Saccharomyces* spp., *Schizosaccharomyces* spp., *Pichia* spp., *Paffia* spp., *Kluyveromyces* spp., *Candida* spp., *Talaromyces* spp., *Brettanomyces* spp., *Pachysolen* spp., *Debaryomyces* spp., and industrial polyploid yeast strains. In certain embodiments the yeast is *S. cerevisiae, K. marxianus, K. lactis, K. thermotolerans, C. sonorensis, C. methanosorbosa, C. diddensiae, C. parapsilosis, C. naeodendra, C. balnkii, C. entomophila, C. shecatae, P. tannophilus* or *P. stipitis*.

Examples of fungi include *Aspergillus* spp., *Pennicilium* spp., *Fusarium* spp., *Rhizopus* spp., *Acremonium* spp., *Neurospora* spp., *Sordaria* spp., *Magnaporthe* spp., *Allomyces* spp., *Ustilago* spp., *Botrytis* spp., and *Trichoderma* spp.

Examples of insect cells include *Spodoptera frugiperda* cell lines such as Sf9 and Sf21, *Drosophila melanogaster* cell lines such as Kc, Ca, 311, DH14, DH15, DH33P1, P2, P4 and SCHNEIDER-2 (D. Mel—S2) and *Lymantria dispar* cedll lines such as 652Y.

Examples of mammalian cells include primary cells, such as stem cells and dendritic cells, and mammalian cell lines such as Vero, HEK 293, Sp2/0, P3UI, CHO, COS, HeLa, BAE-1, MRC-5, NIH 3T3, L929, HEPG2, NS0, U937, HL60, YAC1, BHK, ROS, Y79, Neuro2a, NRK, MCF-10, RAW 264.7, and TBY-2.

Stem cell lines include hESC BG01, hESC BG01V, ES-057BL/6, ES-D3 GL, J1, R1, RW.4, 7AC5/EYFP, and R1/E. Additional human stem cell lines include (NIH designations) CH01, CH02, GE01, GE07, GE09, GE13, GE14, GE91, GE92, SA19, MB01, MB02, MB03, NC01, NC02, NC03, RL05, RL07, RL10, RL13, RL15, RL20, and RL21.

In some embodiments, the cell is engineered or selected (e.g., as described herein) to produce or have altered, optionally increased, production of a molecule of interest (e.g., a $C_4$-$C_6$ heavy alcohol such as isobutanol or isopentanol). In some embodiments, the cell overexpresses one or more genes in a metabolic pathway, e.g., one or more genes involved in the Ehrlich pathway, the acetone-butanol-ethanol (ABE) pathway, and/or the branched chain amino acid (BCAA) pathway (e.g., via the branched chain α-keto acid dehydrogenase complex (BCKDC)). In some embodiments, the cell expresses (or overexpresses) one or more genes (e.g., one or metabolic genes as described herein) from a different organism.

In some embodiments, the cell comprises a deletion or mutation of one or more genes (e.g., one or more regulatory or competing metabolic genes as described herein). For example, a gene encoding a polypeptide that produces a small-molecule regulator of a transcription factor can be mutated to render insensitive to regulation the polypeptide encoded by the gene. An example of this is making mutation(s) in LEU4 to render the Leu4 protein insensitive to leucine. In other examples, the one or more genes that are deleted or mutated are in a competing pathway. Mutations can be single or multiple point mutations, additions, partial internal deletions, N-terminal or C-terminal deletions (truncations), or complete deletions, all of which can affect amino acid sequence encoded the gene(s).

Deletions or mutations can be made using standard methods in the art. Mutations can be non-random, partially random or random, or a combination of these mutations. For example, for a partially random mutation, the mutation(s) may be confined to a certain portion of the nucleic acid molecule encoding a polypeptide in which mutation(s) are to be made.

The method of mutation can be selected based on the type of mutations that are desired. For example, for random mutations, methods such as error-prone PCR amplification of the nucleic acid molecule can be used. Site-directed mutagenesis can be used to introduce specific mutations at specific nucleotides of the nucleic acid molecule. Synthesis of the nucleic acid molecules can be used to introduce specific mutations and/or random mutations, the latter at one or more specific nucleotides, or across the entire length of the nucleic acid molecule. Methods for synthesis of nucleic acids are well known in the art (e.g., Tian et al., *Nature* 432: 1050-1053 (2004)).

DNA shuffling (also known as gene shuffling) can be used to introduce still other mutations by switching segments of nucleic acid molecules. See, e.g., U.S. Pat. No. 6,518,065, related patents, and references cited therein. The nucleic acid molecules used as the source material to be shuffled can be nucleic acid molecule(s) that encode any of the polypeptides described herein. For example, nucleic acid molecules encoding different nuclear receptor-like transcription factors, such as those of a single species or those from different species, can be shuffled.

A variety of other methods of mutating nucleic acid molecules, in a random or non-random fashion, are well known to one of ordinary skill in the art. One or more different methods can be used combinatorially to make mutations in nucleic acid molecules. In this aspect, "combinatorially" means that different types of mutations are combined in a single nucleic acid molecule, and assorted in a set of nucleic acid molecules. Different types of mutations include point mutations, truncations of nucleotides, deletions of nucleotides, additions of nucleotides, substitutions of nucleotides, and shuffling (e.g., re-assortment) of segments of nucleotides. Thus, any single nucleic acid molecule can have one or more types of mutations, and these can be randomly or non-randomly assorted in a set of nucleic acid molecules. For example, a set of nucleic acid molecules can have a mutation common to each nucleic acid molecule in the set, and a variable number of mutations that are not common to each nucleic acid molecule in the set.

In some embodiments, the cell has altered transport of one or more molecules. For example, in some embodiments the altered transport is increased uptake of a precursor of a molecule of interest, decreased export of a molecule of interest, or increased export of a molecule of interest. In some embodiments, the cell is selected or engineered to be resistant to high levels of the molecule of interest or intermediates in synthesis of the molecule of interest.

The cell can include one or more recombinant nucleic acid constructs that collectively include at least two promoters. In such cases, each promoter is operably linked to a different selectable marker, and the promoters are regulated by either (i) different nuclear receptor-like transcription factors, the activity of each of which is regulated by a different small-molecule regulator; or (ii) the same nuclear receptor-like transcription factor, regulated by the same small molecule regulator, but acting on different natural or synthetic promoters with different sensitivities or dynamic ranges.

In the cells described herein, the one or more recombinant nucleic acid constructs can be integrated into the genome and/or exist as non-genomic vectors, such as episomal vectors. In some cases these vectors are low copy number vectors, while in other cases these vectors are high copy number vectors. If there are two or more vectors, the copy number of the vectors can be the same or different.

Compositions that include any of the cells described herein also are provided. The composition also can include one or more factors to be tested.

The factors can be one or more types of small organic molecule and/or one or more genes or gene products. The genes or gene products can be added to the cell, mutated in the cell, overexpressed in the cell, reduced in expression or activity in the cell or deleted from the cell.

In some embodiments, the factor is one or more molecules that regulate one or more genes or gene products, such as a CRISPR-based system for changing gene regulation, including for interference, inhibition, or activation of gene expression. In some embodiments, components of the Type II clustered, regularly interspaced, short palindromic repeats (CRISPR)/CRISPR-associated (Cas) system are used to selectively cleave DNA encoding a gene of interest for changing gene regulation, such as interference with gene expression, inhibition of gene expression, and activation of gene expression. CRISPR-based systems are well known in the art, and aspects of CRISPR-based systems and their application are disclosed, for example, in U.S. Pat. No. 8,361,725; U.S. Pat. No. 8,546,553; US 2008/0124725; US 2010/0076057; US 2010/0093617; US 2011/0189776; US 2013/0330778; WO 2013/098244; WO 2013/176772; WO 2013/188037; Deltcheva et al. Nature. 2011 Mar. 31; 471 (7340):602-7; Jinek et al. Science. 2012 Aug. 17; 337(6096): 816-21; Qi et al. Cell. 2013 Feb. 28; 152(5):1173-83; DiCarlo et al. Nucleic Acids Res. 2013 April; 41(7):4336-43; Gilbert et al. Cell. 2013 Jul. 18; 154(2):442-51; Mali et al. Nat Biotechnol. 2013 September; 31(9):833-8; Mali et al. Nat Methods. 2013 October; 10(10):957-63; Esvelt et al. Nat Methods. 2013 November; 10(11): 1116-21; each of which is incorporated by reference for the subject matter relevant to CRISPR-based systems disclosed therein.

The one or more genes or gene products can be in a pathway that includes the small-molecule regulator that regulates the nuclear receptor-like transcription factor. The one or more genes or gene products can be a nucleic acid or library of nucleic acids that inhibit or activate proteins or that encodes polypeptides that inhibit or activate proteins, such as recombinant single domain antibodies, optionally camelid single domain antibodies. Camelid single domain antibodies, e.g., VHH, are well known in the art.

Also provided herein are methods of making the foregoing cells. The methods include introducing into a cell a nucleic acid construct comprising a promoter operably linked to a selectable marker, wherein the promoter is regulated by a nuclear receptor-like transcription factor, the activity of which is regulated by a small-molecule regulator. In some cases the cell expresses the nuclear receptor-like transcription factor, which regulates the selectable marker depending on the presence or level of the small-molecule regulator. Such methods also include engineering the cell to reduce feedback inhibition of an enzyme that produces the small-molecule regulator, as described elsewhere herein (e.g., for leucine-insensitive Leu4 polypeptides).

Nucleic acid constructs also are provided. The nucleic acid constructs include sequences coding for at least two of the following elements that are describe extensively elsewhere herein:

(1) a promoter operably linked to a selectable marker, wherein the promoter is regulated by a nuclear receptor-like transcription factor, the activity of which is regulated by a small-molecule regulator;
(2) a nuclear receptor-like transcription factor that binds to and regulates transcription by the promoter; and
(3) a gene product that synthesizes the small-molecule regulator or a gene product that is upstream in a pathway of the gene product that synthesizes the small-molecule regulator.

The nucleic acid construct can be a vector, such as a plasmid. In certain embodiments, the plasmid is a high copy number plasmid or a low copy number plasmid. Vectors are well known in the art and may include cloning vectors, expression vectors, etc.

A cloning vector is a recombinant nucleic acid construct which is able to replicate autonomously or integrated in the genome in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is a recombinant nucleic acid construct into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode polypeptides or enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., fluorescent proteins such as green fluorescent protein). Preferred vectors are those capable of autonomous replication and expression of the structural gene products present in the DNA segments to which they are operably joined.

As used herein, a coding sequence and regulatory sequences are said to be "operably" joined or linked when they are covalently linked in such a way as to place the expression or transcription of the coding sequence under the influence or control of the regulatory sequences. If it is desired that the coding sequences be translated into a functional protein, two DNA sequences are said to be operably joined or linked if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined or linked to a coding sequence if the promoter region were capable of effecting transcription of that DNA sequence such that the resulting transcript can be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. In particular, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

In some embodiments, the promoter in the nucleic acid construct comprises one or more UASs for LEU3, such as LEU3 from *S. cerevisiae*. In some embodiments, the nuclear receptor-like transcription factor in the nucleic acid construct is LEU3. In such embodiments, the promoter can be a promoter that is natively regulated by LEU3, such as a LEU1, ILV2, LEU4, BAP2, BAT2 or GDH1 promoter. In some embodiments, the promoter is a *S. cerevisiae* promoter. In some embodiments, the gene product that synthesizes the small-molecule regulator nucleic acid construct is LEU4. In such embodiments, the LEU4 can be a leucine-insensitive LEU4 mutant, such as a LEU4 from *S. cerevisiae* having a mutation or deletion of amino acid Ser547, a deletion of amino acids 411-619, a deletion of amino acids 424-619, a mutation of Gly514 or Gly516 to aspartic acid, a mutation of Ala552 to threonine, a mutation of Glu540 to lysine, a mutation of His541 to proline, a mutation of Ser519 to threonine, and a mutation of Asp578 to tyrosine.

Methods for screening for factors that affect metabolic pathways also are provided. The methods include: 1) (a) providing any of the foregoing cells or a composition including such cells, and introducing a factor to be screened into the cell or contacting the cell with a factor to be screened, or (b) providing a composition including any of the foregoing cells and a factor to be tested; and 2) detecting a gene product of the selectable marker. An increase or decrease of the gene product of the selectable marker indicates that the factor is one that affects a metabolic pathway.

"Introducing a factor to be screened into the cell" includes introducing into a cell or cells one or more recombinant nucleic acid constructs using methods and techniques that are standard in the art. For example, recombinant nucleic acid constructs can be introduced by various transfection methods, transduction, electroporation, particle bombardment, injection (including microinjection of cells and injection into multicellular organisms), lipofection, yeast spheroplast/cell fusion for YACs (yeast artificial chromosomes), Agrobacterium-mediated transformation for plant cells, etc. Methods for transforming yeast strains are described in WO 99/14335, WO 00/71738, WO 02/42471, WO 03/102201, WO 03/102152, and WO 03/049525.

"Introducing a factor to be screened into the cell" also may be accomplished by integrating one or more recombinant nucleic acid constructs into the genome of a cell or by replacing one or more nucleic acid sequences with mutated sequence(s) using one or more recombinant nucleic acid constructs.

Thus in some embodiments, "introducing a factor to be screened into the cell" includes mutagenizing one or more endogenous gene(s) of the cell, such as by with UV or chemical mutagenesis, or any of the other methods of mutagenesis known in the art such as those described elsewhere herein. The selectable marker can be detected by detecting a gene product of the selectable marker or by detecting a result of the expression of the selectable marker according to standard assays, some of which are described herein (e.g., for fluorescent protein expression and for kanamycin resistance). Other assays for detecting nucleic acid or polypeptide gene products of selectable markers are well known in the art. In some embodiments, an increase of the gene product of the selectable marker indicates that the factor increases synthesis of a molecule of interest produced by the pathway and/or increases flux through the pathway.

The factor can be one or more types of small organic molecule and/or can be one or more genes or gene products that is/are added to the cell, mutated in the cell, overexpressed or activated in the cell, reduced in expression or activity in the cell or deleted from the cell. Combinations and libraries of factors can be screened using the methods described herein.

In some embodiments, the factor is one or more molecules that regulate one or more genes or gene products, such as a CRISPR-based system for changing gene regulation, as described elsewhere herein.

In some embodiments, the one or more genes or gene products is in a pathway that includes the small-molecule regulator that regulates the nuclear receptor-like transcription factor. In other embodiments, the one or more genes or gene products is a nucleic acid or library of nucleic acids that inhibit or activate proteins or that encodes polypeptides that inhibit or activate proteins, such as recombinant single domain antibodies, optionally camelid single domain antibodies.

If the factor is a gene or gene product is mutated in the cell or added to the cell, then the method can also include isolating at least a portion of the gene, optionally sequencing at least the portion of the gene, and/or optionally introducing the mutated or added gene into a different cell. Techniques for isolating, sequencing and introducing the mutated or added gene into a different cell are well known to those skilled in the art.

A factor identified as one that affects a metabolic pathway is a factor that increases synthesis or reduces degradation of a molecule that is a product, an intermediate or a side product of the metabolic pathway. Thus the factor may be one that increases synthesis of a molecule that is a product of the metabolic pathway, or one that reduces degradation of a molecule that is a product of the metabolic pathway. The factor may be one that results in increased levels of a molecule that is a product of the metabolic pathway. Such molecules may be the product that is desired, or a precursor thereof, or an intermediate in the synthesis thereof.

In other embodiments, the factor identified as one that affects a metabolic pathway is a factor that reduces synthesis or increases degradation of a molecule that is a product, an intermediate or a side product of the metabolic pathway.

In various embodiments the molecule of interest may be one that is retained in the cell or one that is secreted by the cell. Thus the factor identified as one that affects a metabolic pathway may be a factor that increases or decreases export of a molecule from the cell that is a product, an intermediate or a side product of the metabolic pathway.

The factor identified as one that affects a metabolic pathway also can be a factor that improves of alters substrate utilization, or allows use of one or more different substrate(s). Substrates in this context include sugars and other carbon sources that are typically used in fermentation, including 6-carbon and 5-carbon sugars. Substrates also may include molecules that are utilized by only a subset of metabolic pathways of the cells.

The methods also can include detecting, measuring or isolating the molecule that is a product, an intermediate or a side product of the metabolic pathway.

The metabolic flux biosensors described herein can use the small-molecule regulator that regulates the nuclear receptor-like transcription factor in the cell as a proxy for synthesis of a different molecule. For example, the small-molecule regulator alpha-isopropylmalate, is a proxy for synthesis of branched-chain amino acids, $\alpha$-keto acids, alcohols, aldehydes, or other products derived from these compounds. Other metabolic pathways will have other small-molecule regulator that regulates the nuclear receptor-like transcription factors that can serve as proxies for synthesis of different molecules, such as intermediates and final products of the metabolic pathways.

In addition to the branched-chain amino acids (leucine) biosynthetic pathway shown and exemplified herein, other metabolic pathways that may be used to design metabolic flux biosensors. These include, without limitation, pathways for the synthesis of small amino acids, histidine and aspartate amino acid groups, aromatic amino acids, glutamate amino acid group, isobutanol, isopentanol, proline, pyrimidines, purines, fatty acids, urea, secondary metabolites including isoprenoids, polyketides and alkaloids, as well as the pentose phosphate pathway, acetone-butanol-ethanol pathway, Ehrlich pathway, citric acid cycle, synthesis pathway, and fermentation pathways. Other metabolic pathways include pathways that synthesize heme, tetrahydrofolate, pantothenic acid, ubiquinone, steroids, aminolevulinic acid, biotin, lipoic acid, and $\alpha$-keto acids, (including $\alpha$-ketoisovalerate and $\alpha$-keotisocaproate). The products and intermediates of such metabolic pathways are well known in the art, and can include molecules of commercial interest and importance in their own rights or as precursors of other molecules.

Also provided herein are methods for producing a molecule produced by a metabolic pathway. The methods include providing a cell that comprises a factor identified in any of the foregoing methods or that is contacted with a factor identified in any of the foregoing methods, and culturing the cell under suitable conditions for a time sufficient to produce the molecule. The methods further can include isolating the molecule from the cells, from the culture, or from medium in which the cell is or was cultured.

Methods also are provided for screening for cells that have a selected metabolic pathway or that have an alteration in a selected metabolic pathway, such as an alteration that results in increased synthesis or level of a molecule of interest. The methods include 1) (a) providing a cell, and introducing into the cell any of the foregoing recombinant nucleic acid constructs, wherein the promoter operably linked to the selectable marker is regulated by a nuclear receptor-like transcription factor that is in the selected metabolic pathway or a nuclear receptor-like transcription factor that is regulated by a small-molecule regulator of the selected metabolic pathway, or (b) providing a cell that includes any of the foregoing recombinant nucleic acid constructs; and 2) detecting a gene product of the selectable marker. The gene product of selectable marker indicates that the cell is one that has the selected metabolic pathway. The selectable marker can be detected, for example, by detecting a gene product of the selectable marker or by detecting a result of the expression of the selectable marker, as described elsewhere herein.

In any of the methods described herein, a plurality of factors (such as nucleic acid constructs, small molecules, etc.) can be introduced into a plurality of cells and cells can be identified that have an increased level of the gene product of the selectable marker relative to other cells.

Methods for producing a molecule produced by a metabolic pathway also are provided. Such methods include providing a cell identified by the foregoing methods for screening for cells that have a selected metabolic pathway, and culturing the cell under suitable conditions for a time sufficient to produce the molecule. Such methods also can include isolating the molecule from the cells, from the culture, or from medium in which the cell is or was cultured.

The molecule produced by the cell can be a metabolite. As used herein, a "metabolite" is any molecule that is made or can be made in a cell. Metabolites include metabolic intermediates or end products, any of which may be toxic to the cell, in which case the increased production may involve tolerance of the toxic metabolite. Thus metabolites include small molecules, peptides, large proteins, lipids, sugars, etc. Exemplary metabolites include amino acids; alcohols including ethanol and heavy alcohols; therapeutic proteins, such as antibodies or antibody fragments.

In some cases, cells are used that were previously optimized for a predetermined phenotype prior to use in the methods described herein. Thus, in the production of an alcohol, for example, rather than starting with a cell that produces only a small amount of the alcohol, one can preferentially use a cell that produces a higher amount of the alcohol, such as an optimized amount of the alcohol. In such cases, the methods described herein are used to further improve an already-improved phenotype.

As another example, a yeast can be used that is genetically engineered to express or overexpress (relative to wild type levels) one or more proteins that confer an increased ability to take up or metabolize a sugar. The sugar may be, e.g., a monosaccharide, disaccharide, or oligosaccharide. The sugar may be one that is not normally utilized in significant amounts by the yeast. The sugar may be xylose, arabinose, etc. A number of approaches are known in the art to engineer yeast for xylose metabolism. See, e.g., Jeffries, et al., *Curr. Op. Biotechnol.*, 17: 320-326, 2006 and references therein, which are incorporated herein by reference. The yeast may be engineered to carry out the pentose phosphate pathway (PPP), the biochemical route for xylose metabolism found in many organisms. Suitable proteins include, but are not limited to, xylose reductase, xylitol dehydrogenase, phosphoketolase, and transporters or permeases that facilitate substrate entry into cells. In certain embodiments the yeast is able to metabolize at least two sugars to ethanol, e.g., glucose and xylose.

Standard cell culture or fermentation methods can be used in the present invention. For example, cells of the invention are cultured in a fermentation medium that includes a suitable sugar or sugars. In certain embodiments the sugars are hydrolysates of a cellulose- or hemicelluose-containing biomass. The fermentation medium may contain other sugars as well, notably hexose sugars such as dextrose (glucose) fructose, oligomers of glucose such as maltose, maltotriose and isomaltotriose, and panose. In case of oligomeric sugars, enzymes may be added to the fermentation broth in order to digest these to the corresponding monomeric sugar. The medium will typically contain nutrients as required by the particular cell including a source of nitrogen (such as amino acids proteins, inorganic nitrogen sources such as ammonia or ammonium salts, and the like), and various vitamins, minerals and the like. Other fermentation conditions, such as temperature, cell density, selection of substrate(s), selection of nutrients, etc., may be selected as known in the art. Temperatures during each of the growth phase and the production phase may, in certain embodiments, range from above the freezing temperature of the medium to about 50 degrees C. The optimal temperature may be selected based on the particular cell being used. Culturing can be conducted continuously, batch-wise, or some combination thereof.

EXAMPLES

In order that the invention described herein may be more fully understood, the following examples are set forth. It should be understood that these examples are for illustrative purposes only and are not to be construed as limiting this invention in any manner.

Example 1

Design and Construction of a Leu3 Biosensor

Metabolic engineering is hindered by the lack of high throughput screen technologies, for example for assessing production of heavy alcohols. Metabolic flux biosensors as described herein provide useful tools for indirect quantification of a product, using production of a reporter molecule as a proxy for the desired product.

With the goal of developing yeast strains for robust heavy alcohol production, a biosensor was designed to induce expression of a reporter gene product (e.g., GFP, YFP, etc.) as a measure of production of an intermediate of the leucine biosynthetic pathway shared by the isopentanol pathway, thus serving as a proxy for alcohol production.

To test this concept, *S. cerevisiae* was engineered to express a metabolic flux biosensor that harnesses the capacity of Leu3 to regulate the branched chain amino acid (BCA) biosynthesis pathway. As depicted in FIG. 1, the BCA pathway provides 2-ketoisovalerate as a substrate for Leu4 that produces α-isopropylmalate (α-IPM), which is an intermediate for both production of leucine and isopentanol. When the BCA pathway is on, in the absence of leucine, α-IPM binds the dual function nuclear receptor-like transcription factor, Leu3. α-IPM-bound Leu3 functions as an activator for many genes in the leucine biosynthetic pathway including leu1, leu2, bat1, and bat2, thus promoting production of α-keto-isocaproate which can be used to synthesize leucine and isopentanol. The leucine biosynthetic pathway is end-product inhibited, such that when leucine is present and the BCA system is off, leucine binds to Leu4 and inhibits its catalytic activity and thus α-IPM is not produced. In the unbound state, Leu3 functions as a repressor for the same genes of the leucine biosynthetic pathway it activated when bound by α-IPM.

This exemplary embodiment describes the generation of a biosensor that using the regulatory capacity of Leu3 to assess α-IPM production as a proxy for both leucine and heavy alcohol production in a cell.

Figure 2:
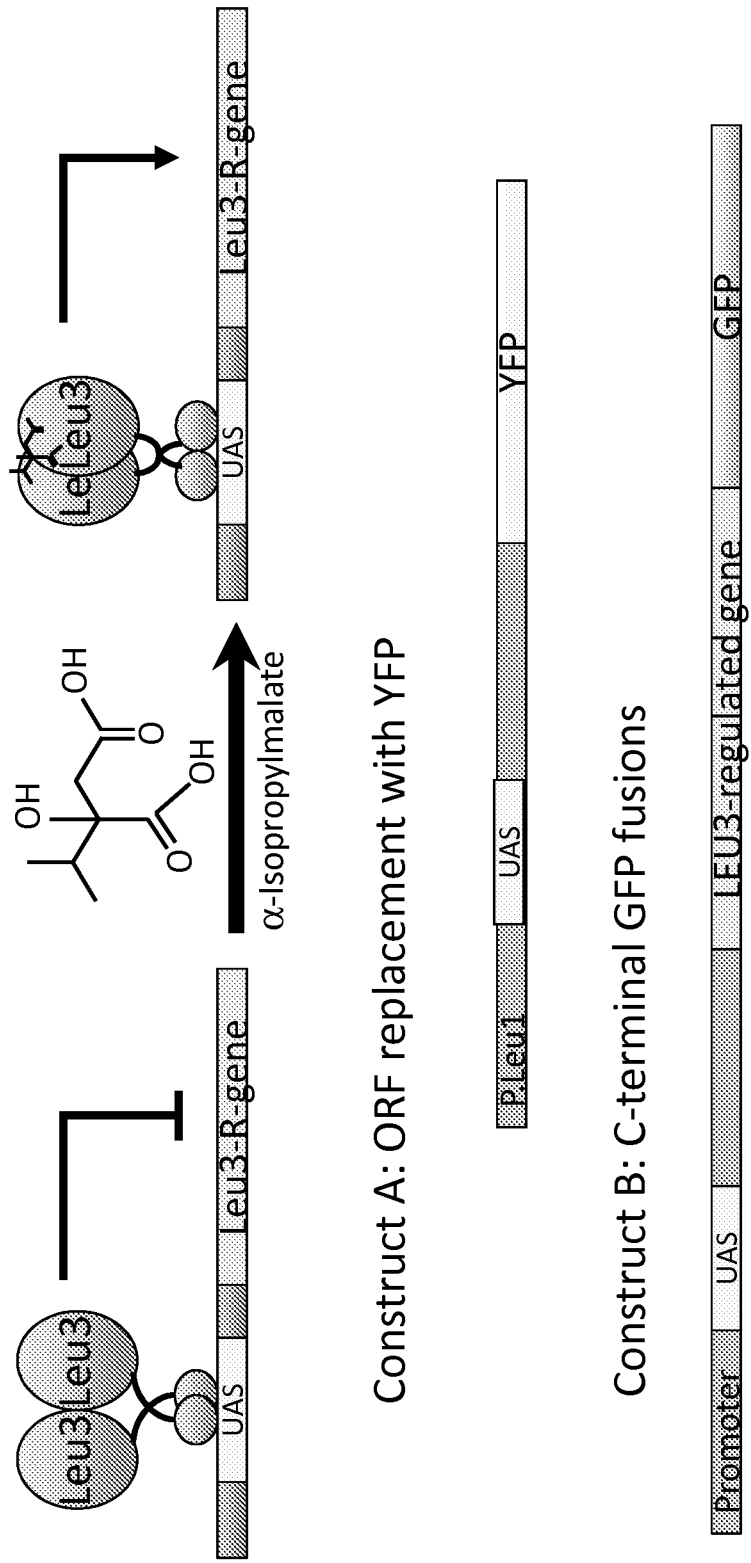
FIG. 2 depicts a schematic representation of regulation of gene expression by Leu3 protein and a metabolic flux biosensor regulated by Leu3. In the absence of the intermediate α-IPM, Leu3 functions as a repressor and inhibits expression of the Leu3-regulated gene (Leu3-R-gene). In the presence of α-IPM, Leu3 induces expression of the Leu3-R-gene. Construct A shows an exemplary construct design in which the open reading frame (ORF) of the Leu3-regulated gene is replaced by a selectable marker (e.g. a reporter gene, in this case yellow fluorescent protein (YFP)) under control of the Leu3-regulated promoter containing an upstream activating sequence (UAS). Construct B shows an alternative exemplary construct design in which a selectable marker (e.g. a reporter gene, in this case green fluorescent protein (GFP)) is expressed as a C-terminal fusion to a Leu3-regulated gene under control of the Leu3-regulatable promoter including a UAS.

Several distinct biosensor constructs were designed to test the Leu3 regulatory system. As schematically depicted in FIG. 2, in a cell, Leu3 that is not bound to α-IPM acts as a repressor on Leu3-regulated genes, but when bound to α-IPM, Leu3 is able to activate the promoters of Leu3-regulated genes and induce expression of the Leu3-regulated gene products. For use in the biosensor constructs, promoters for LEU1, ILV2, LEU4, LEU1, BAP2, BAT2 and GDH1 were tested for responding in parallel with leucine pathway induction. LEU1 promoter had the best response and thus was used in all biosensor constructs. Construct A utilizes the Leu1 promoter sequence including the upstream activating sequence (UAS) and is operably linked to the sequence of the YFP reporter gene. This construct results in complete replacement of the open reading frame (ORF) of the Leu1 gene. Alternatively, Construct B, also depicted in FIG. 2, utilizes a Leu3-regulated promoter from Leu1 but maintains the Leu1 ORF. The reporter gene (GFP) is fused downstream of the Leu1 ORF and the product is a C-terminal fusion of GFP to Leu1 protein. Both constructs rely on Leu3 activity and α-IPM production for expression of the reporter gene from the Leu1 promoter.

Example 2

Proof of Concept of Leu3 Biosensor

Figure 3:
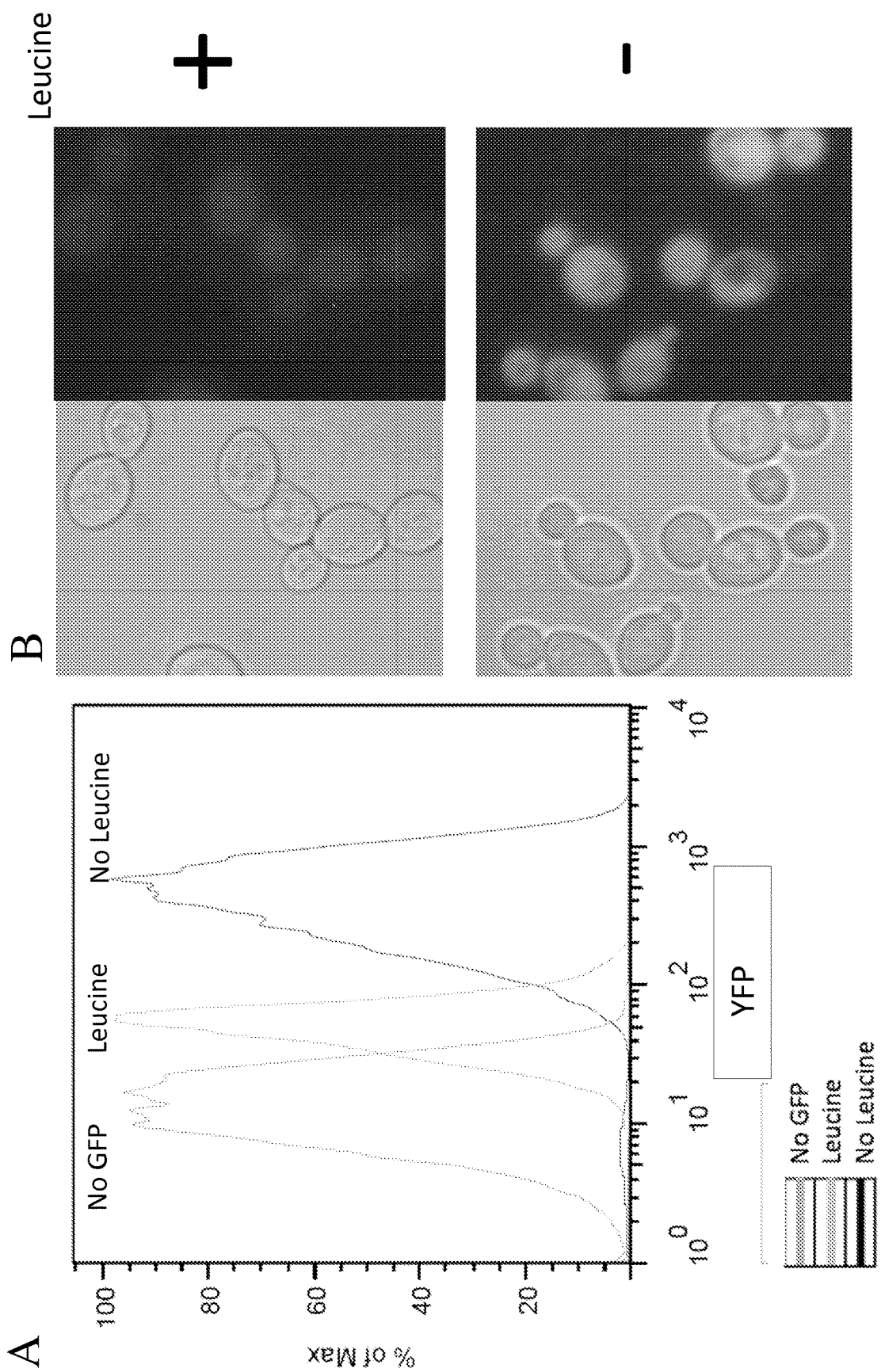
FIG. 3A and FIG. 3B show expression of the Leu3-regulated biosensor Construct A in S. cerevisiae.

Both biosensor constructs, Construct A and Construct B, were cloned onto independent plasmids and introduced into *S. cerevisiae* cells. To test whether the biosensor constructs were regulated by Leu3, cultures of *S. cerevisiae* cells encoding Construct A and *S. cerevisiae* cells encoding Construct B each were grown in the presence of leucine in the culture medium or in the absence of leucine, then assessed by flow cytometry or fluorescence microscopy. As demonstrated in FIGS. 3 and 4, both biosensors were activated in the absence of leucine as indicated by the robust production of the respective reporter protein, YFP or GFP. When the medium was supplemented with leucine, there was minimal detection of the fluorescent reporter proteins, evidencing repression of the reporter gene in a manner similar to the endogenous Leu3-regulated genes. The biosensor of Construct A resulted in a higher mean fluorescence intensity but also resulted in higher background fluorescence in the absence of leucine as seen in both flow cytometry analysis as well as by fluorescence microscopy (FIG. 3). The biosensor of Construct B resulted in lower background fluorescence in the absence of leucine but did not achieve the same maximal intensity of that of Construct A.

Example 3

Optimization of the Leu3 Biosensor

As abovementioned, the leucine biosynthetic pathway is end-product inhibited such that leucine binds and inhibits the catalytic activity of Leu4, preventing α-IPM production. In order to alleviate the leucine sensitivity of the system that may inhibit maximal synthesis of the desired product, a leucine insensitive Leu4 mutant was generated by deletion of S547 and this Leu4 mutant was introduced into *S. cerevisiae* encoding the Leu3 biosensor on an overexpression vector.

Figure 5:
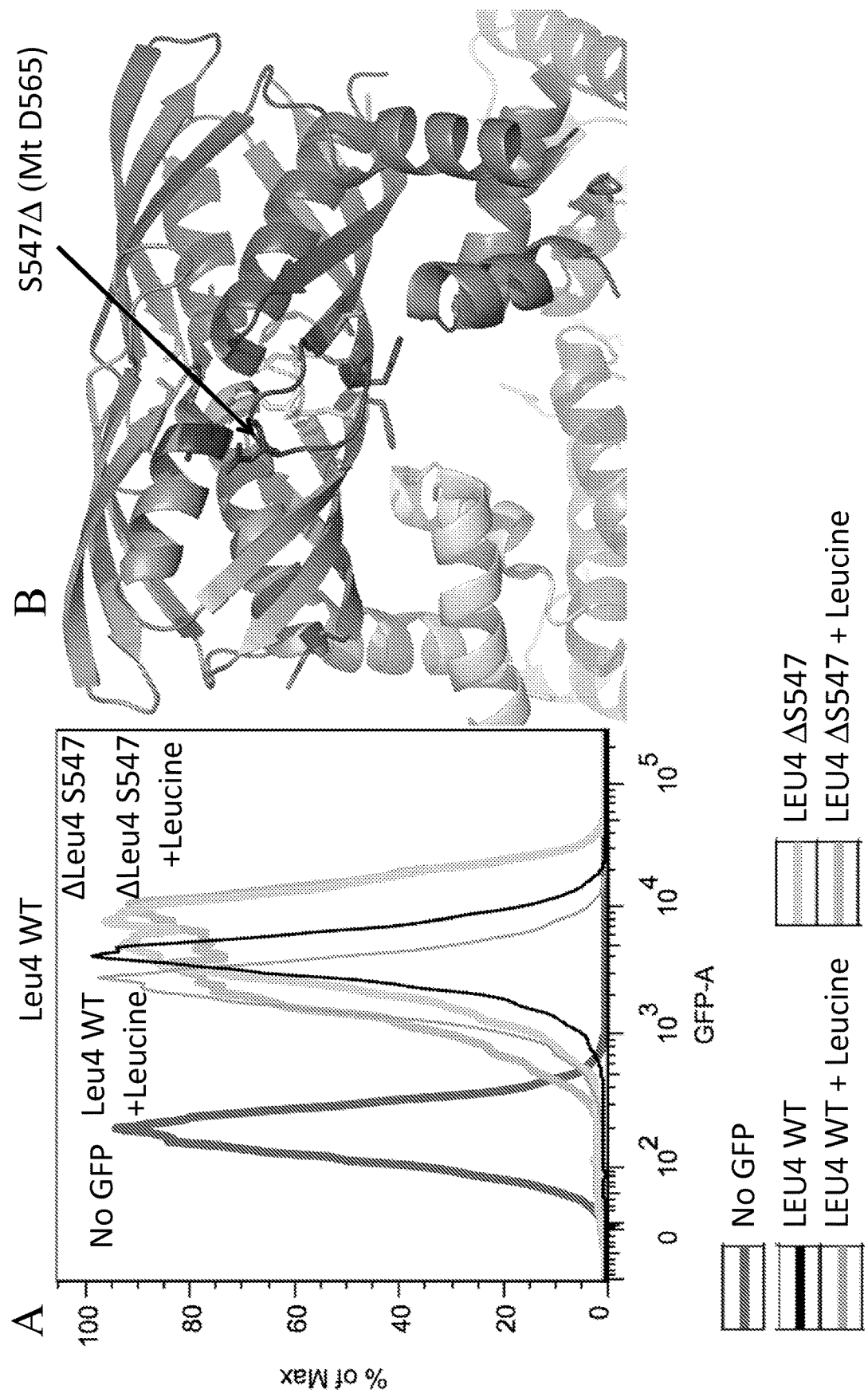
FIG. 5A and FIG. 5B show the activity of a biosensor expressed in S. cerevisiae expressing a mutant Leu4 protein.

*S. cerevisiae* strains encoding the Leu3 biosensor and either only wild-type Leu4 or wild-type Leu4 and the dominant S547 Leu4 mutant were cultured in the presence or the absence of leucine and analyzed for expression of the reporter protein. As shown in FIG. 5A, expression of the biosensor in the *S. cerevisiae* strain expressing only wild-type Leu4 was induced in the absence of leucine but repressed when leucine was added to the medium. In contrast, expression of the biosensor in the *S. cerevisiae* strain expressing Leu4ΔS547 was induced in both the presence and the absence of leucine. This indicated that the mutant Leu4 allele remained active and able to produce α-IPM regardless of the addition of leucine and despite the presence of wild-type Leu4.

With the goal of achieving a leucine-insensitive mutant that is more readily over-expressed, purified and characterized enzymatically, Leu4 truncation mutants were generated that were deficient for the regulatory domain and comprised residue 1-410 (SEQ ID NO: 2) and 1-423 (SEQ ID NO: 3) of the Leu4 protein (wild-type Leu4 protein is 619 amino acids in length, SEQ ID NO:1).

```
                                                SEQ ID NO: 1
Saccharomyces cerevisiae full length Leu4
MVKESIIALAEHAASRASRVIPPVKLAYKNMLKDPSSKYKPFNAPKLSNR

KWPDNRITRAPRWLSTDLRDGNQSLPDPMSVEQKKEYFHKLVNIGFKEIE

VSFPSASQTDFDFTRYAVENAPDDVSIQCLVQSREHLIKRTVEALTGAKK

ATIHTYLATSDMFREIVFNMSREEAISKAVEATKLVRKLTKDDPSQQATR

WSYEFSPECFSDTPGEFAVEICEAVKKAWEPTEENPIIFNLPATVEVASP

NVYADQIEYFATHITEREKVCISTHCHNDRGCGVAATELGMLAGADRVEG

CLFGNGERTGNVDLVTVAMNMYTQGVSPNLDFSDLTSVLDVVERCNKIPV

SQRAPYGGDLVVCAFSGSHQDAIKKGFNLQNKKRAQGETQWRIPYLPLDP

KDIGRDYEAVIRVNSQSGKGGAAWVILRSLGLDLPRNMQIEFSSAVQDHA

DSLGRELKSDEISKLFKEAYNYNDEQYQAISLVNYNVEKFGTERRVFTGQ

VKVGDQIVDIEGTGNGPISSLVDALSNLLNVRFAVANYTEHSLGSGSSTQ

AASYIHLSYRRNADNEKAYKWGVGVSEDVGDSSVRAIFATINNIIHSGDV

SIPSLAEVEGKNAAASGSA
```

SEQ ID NO: 2
Saccharomyces cerevisiae Leu4 truncation (residues
1-410)
MVKESIIALAEHAASRASRVIPPVKLAYKNMLKDPSSKYKPFNAPKLSNR

KWPDNRITRAPRWLSTDLRDGNQSLPDPMSVEQKKEYFHKLVNIGFKEIE

VSFPSASQTDFDFTRYAVENAPDDVSIQCLVQSREHLIKRTVEALTGAKK

ATIHTYLATSDMFREIVFNMSREEAISKAVEATKLVRKLTKDDPSQQATR

WSYEFSPECFSDTPGEFAVEICEAVKKAWEPTEENPIIFNLPATVEVASP

NVYADQIEYFATHITEREKVCISTHCHNDRGCGVAATELGMLAGADRVEG

CLFGNGERTGNVDLVTVAMNMYTQGVSPNLDFSDLTSVLDVVERCNKIPV

SQRAPYGGDLVVCAFSGSHQDAIKKGFNLQNKKRAQGETQWRIPYLPLDP

KDIGRDYEAV

SEQ ID NO: 3
Saccharomyces cerevisiae Leu4 truncation (residues
1-423)
MVKESIIALAEHAASRASRVIPPVKLAYKNMLKDPSSKYKPFNAPKLSNR

KWPDNRITRAPRWLSTDLRDGNQSLPDPMSVEQKKEYFHKLVNIGFKEIE

VSFPSASQTDFDFTRYAVENAPDDVSIQCLVQSREHLIKRTVEALTGAKK

ATIHTYLATSDMFREIVFNMSREEAISKAVEATKLVRKLTKDDPSQQATR

WSYEFSPECFSDTPGEFAVEICEAVKKAWEPTEENPIIFNLPATVEVASP

NVYADQIEYFATHITEREKVCISTHCHNDRGCGVAATELGMLAGADRVEG

CLFGNGERTGNVDLVTVAMNMYTQGVSPNLDFSDLTSVLDVVERCNKIPV

SQRAPYGGDLVVCAFSGSHQDAIKKGFNLQNKKRAQGETQWRIPYLPLDP

KDIGRDYEAVIRVNSQSGKGGAA

Figure 6:
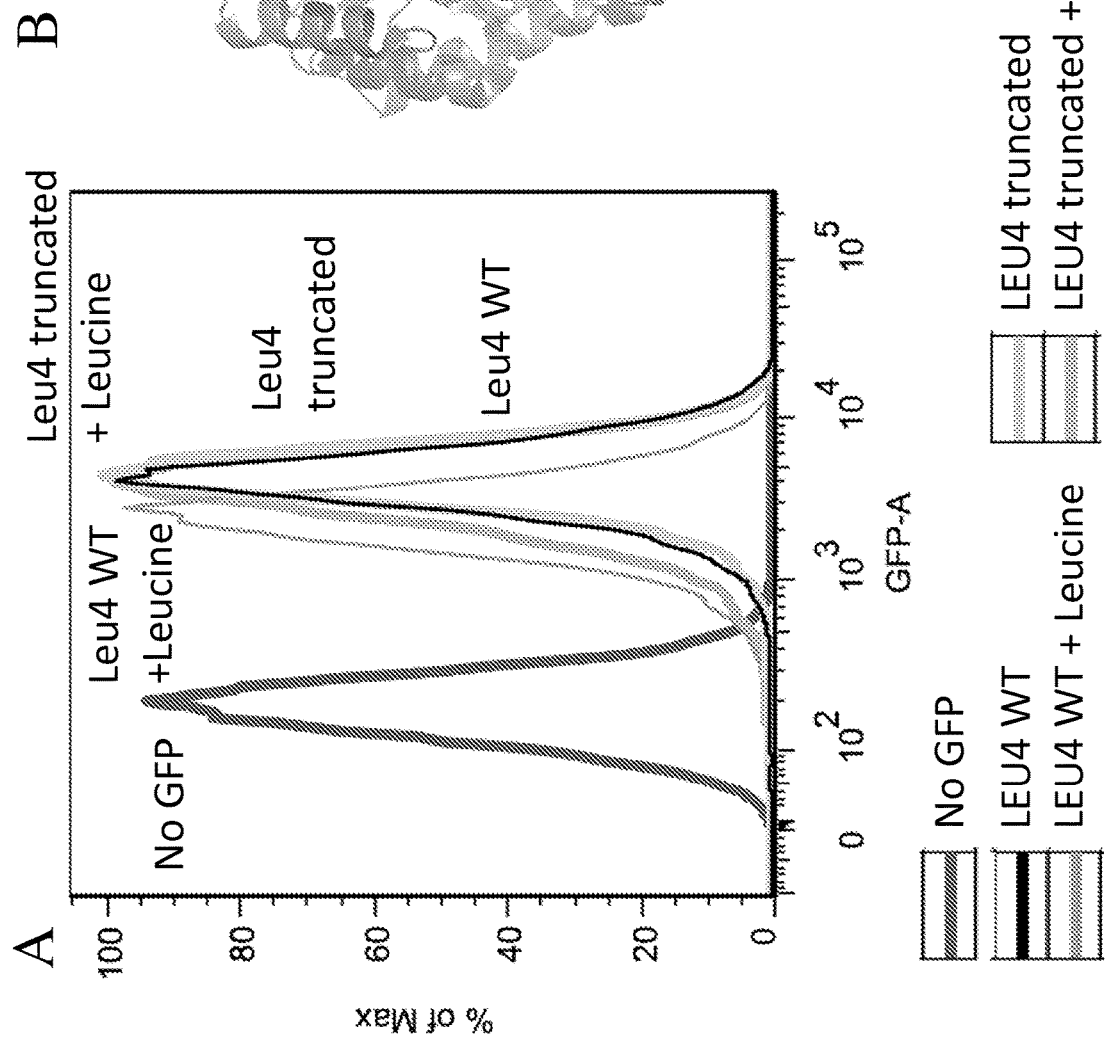
FIG. 6A and FIG. 6B show activity of a biosensor expressed in S. cerevisiae expressing a mutant Leu4 protein.

Leu4 truncations were cloned into overexpression vectors and introduced into *S. cerevisiae* encoding the Leu3 biosensor. The truncated Leu4 protein retained its catalytic activity to produce α-IPM but was non-responsive to leucine. As shown in FIG. 6, the biosensor in the *S. cerevisiae* strain expressing the truncated Leu4 protein was expressed comparably in the presence or the absence of leucine, in contrast to the biosensor of the strain expressing the wild-type Leu4, which was repressed in the presence of leucine.

In order to utilize the biosensor for high throughput screening techniques, the system preferably has a large dynamic range in which to evaluate differences in expression of the selectable marker in the screening conditions. In an effort to improve the dynamic range of the system, two approaches were taken: (1) strains were cultured in the presence of increasing concentrations of exogenous α-IPM, and (2) Leu3 was over-expressed by placing the transcriptional regulator under control of the constitutive Gdp1 (TDH3) promoter.

Figure 10:
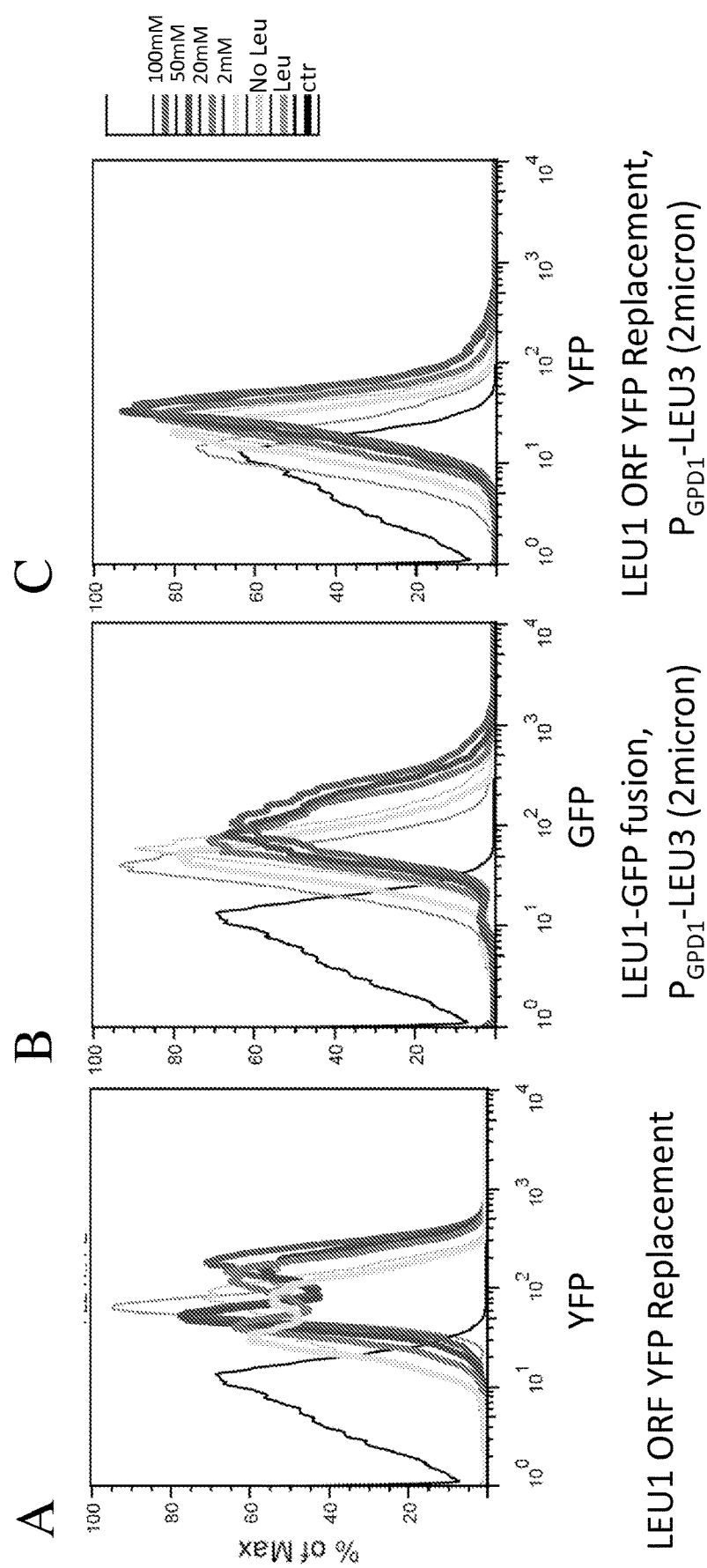
FIGS. 10A-10C shows activity of the biosensors in the presence of the indicated concentrations of α-IPM by flow cytometry analysis.

First, a *S. cerevisiae* strain comprising the Construct A biosensor, as depicted in FIG. 2, was grown in the absence or presence of leucine, or in the presence of leucine with increasing concentrations of exogenous α-IPM. Expression of the reporter protein was assessed by fluorescence microscopy and flow cytometry methods (FIGS. 7 and 10A). The trend demonstrates that despite the presence of leucine in the culture, the reporter expression increased as the α-IPM concentration increased. Importantly, the biosensor expression in the presence of leucine and 100 mM α-IPM was higher than in the absence of leucine, indicating the dynamic range of the biosensor with exogenous α-IPM exceeded that caused simply by the absence of leucine.

Figure 8:
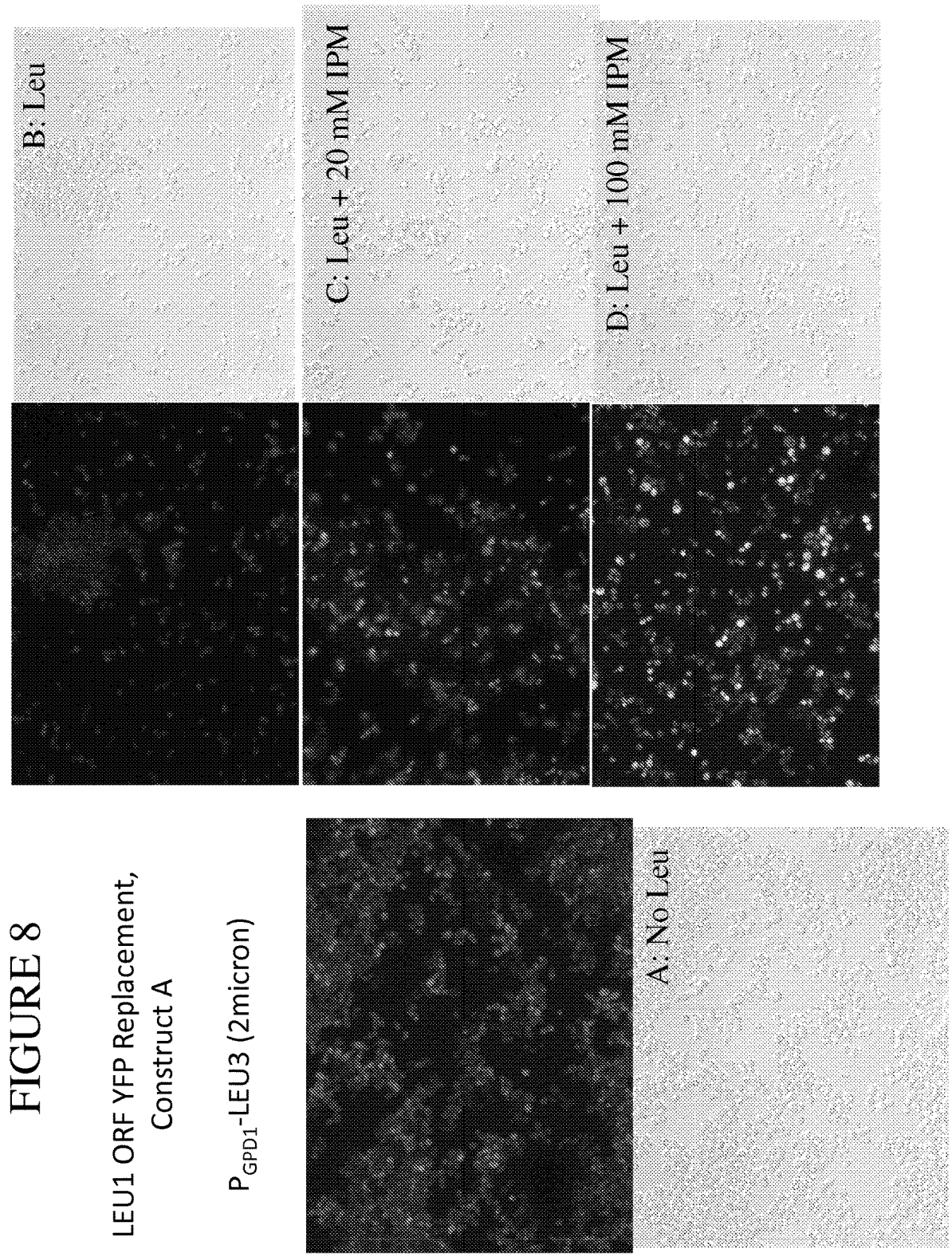
FIGS. 8A-8D show activity of the biosensor Construct A in S. cerevisiae over-expressing Leu3 in the presence of various concentrations of α-IPM.
Figure 9:
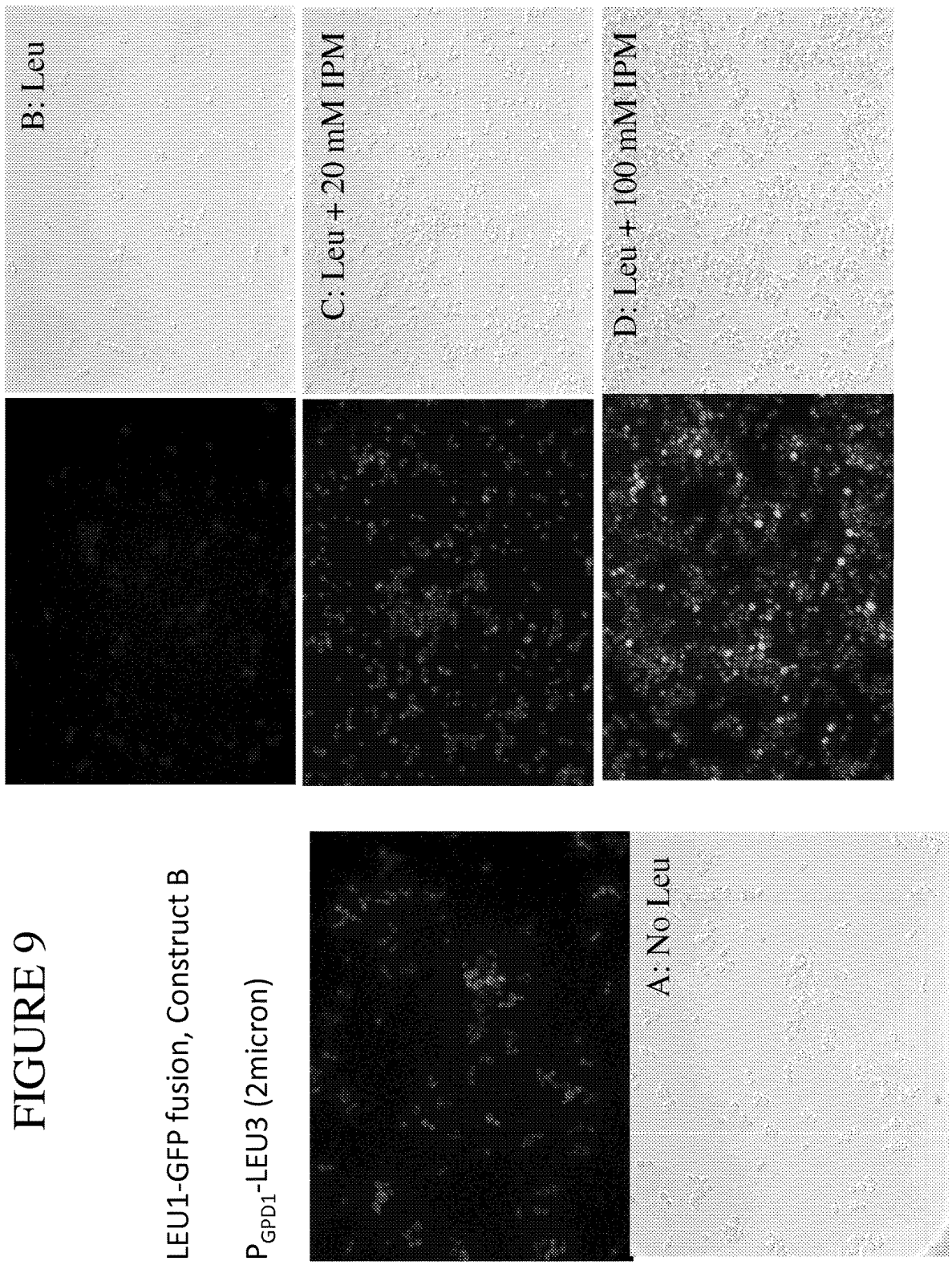
FIGS. 9A-9D show activity of the biosensor Construct B in S. cerevisiae over-expressing Leu3 in the presence of various concentrations of α-IPM.

Next, a *S. cerevisiae* strain comprising Construct A and Leu3 over-expressed by the Gpd1 (TDH3) promoter was cultured in the absence or presence of leucine, or in the presence of leucine with increasing concentrations of exogenous α-IPM. Expression of the reporter protein was assessed by fluorescence microscopy and flow cytometry methods (FIGS. 8 and 10B). A similar trend was seen as for the strains encoding Construct A without Leu3 over-expression (FIGS. 7 and 10A), in that the reporter expression increased as the α-IPM concentration increased, but these results indicated that, in addition to exogenous α-IPM, over-expression of Leu3 can further increase the dynamic range of the system. Interestingly, the fluorescence of the cells of the culture with leucine and 100 mM α-IPM was not homogenous. This is likely due to heterogeneous expression of Leu3 which was provided under control of the Gpd1 (TDH3) promoter on a multicopy plasmid that may result in different levels of expression of Leu3 in different cells. Similar results were attained with *S. cerevisiae* strains encoding Construct B and Leu3 under control of the Gpd1 (TDH3) promoter, although with a lower maximal intensity (FIGS. 9 and 10C).

In addition to over-expressing the transcription factor Leu3, the Leu3-regulated promoter that is used to control expression of the selectable marker may also be engineered, for example to bind two, three or more Leu3 dimers with the goal of further increasing the dynamic range of the bio sensor system.

Figure 19:
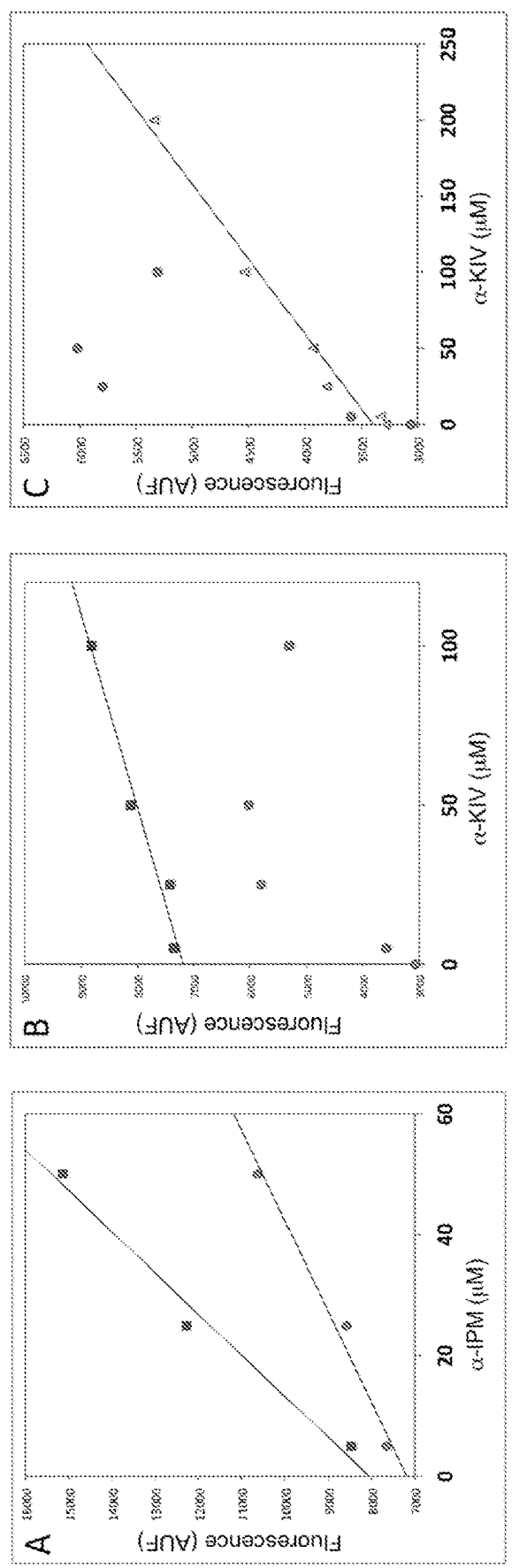
FIGS. 19A-19C show exemplary biosensor responses to intermediate metabolites of branchec-chain amino acid (BCA) biosynthesis.

The biosensor constructs were also assessed to determine if the constructs could respond to supplementation of metabolic intermediates from the BCA pathway. A *S. cerevisiae* strain comprising Construct A was cultured in 10 ml minimal medium with 2% glucose in the presence of increasing concentrations of α-IPM. Cell fluorescence was measured during the exponential cell growth phase. Both biosensor Construct A and biosensor Construct B responded linearly to α-IPM concentrations of up to at least 50 mM (FIG. 19A).

Supplementation of another intermediate metabolite of BCA biosynthesis, α-KIV, was also tested for induction of the biosensors. α-KIV sits at the metabolic fork between isobutanol and isopentanol biosynthesis, and is both a direct precursor of isobutanol and the substrate of Leu4 (see FIG. 1). As shown in FIG. 19B, both biosensor Construct A and biosensor Construct B responded to concentrations of up to at least 100 mM α-KIV in the culture media. The response of the biosensor Construct B can be extended to at least 200 mM of α-KIV by expressing the biosensor in a yeast strain carrying the leucine-insensitive LEU4 mutant allele, thus converting it into a leucine-independent LEU4 biosensor (FIG. 19C). These results show that the biosensors respond to metabolic perturbations on the BCA biosynthetic pathway at the key positions flanking the metabolic fork between isobutanol and isopentanol production. Furthermore, the results show that the sensitivity and dynamic range of the biosensors can be adjusted by modifying the design of the biosensor constructs (e.g., Construct A type vs. Construct B type), or the system (e.g., leucine dependent vs leucine independent LEU4).

Example 4

Selection, Sorting and Enrichment of Cells with Increased Production

Following generation of Leu3 biosensors optimized to achieve a large dynamic range for high throughput screening, methods were developed to select, sort and enrich for cells that display the desired phenotype (e.g., enhanced production of alcohols).

As exemplified in FIG. 11, following transformation of a biosensor into a strain or following mutagenesis, cultures were spread on a solid culture medium and allowed to form colonies. Expression of the reporter protein can be assessed by visualizing the colonies on the solid medium under conditions appropriate for quantifying the reporter protein (e.g., fluorescence scanning for proteins like GFP). Colonies with the desired phenotype, including increased or decreased reporter activity, can be selected for amplification or, in the case of mutagenesis, sequencing to identify additional mutations that may influence production of the desired product.

Figure 12:
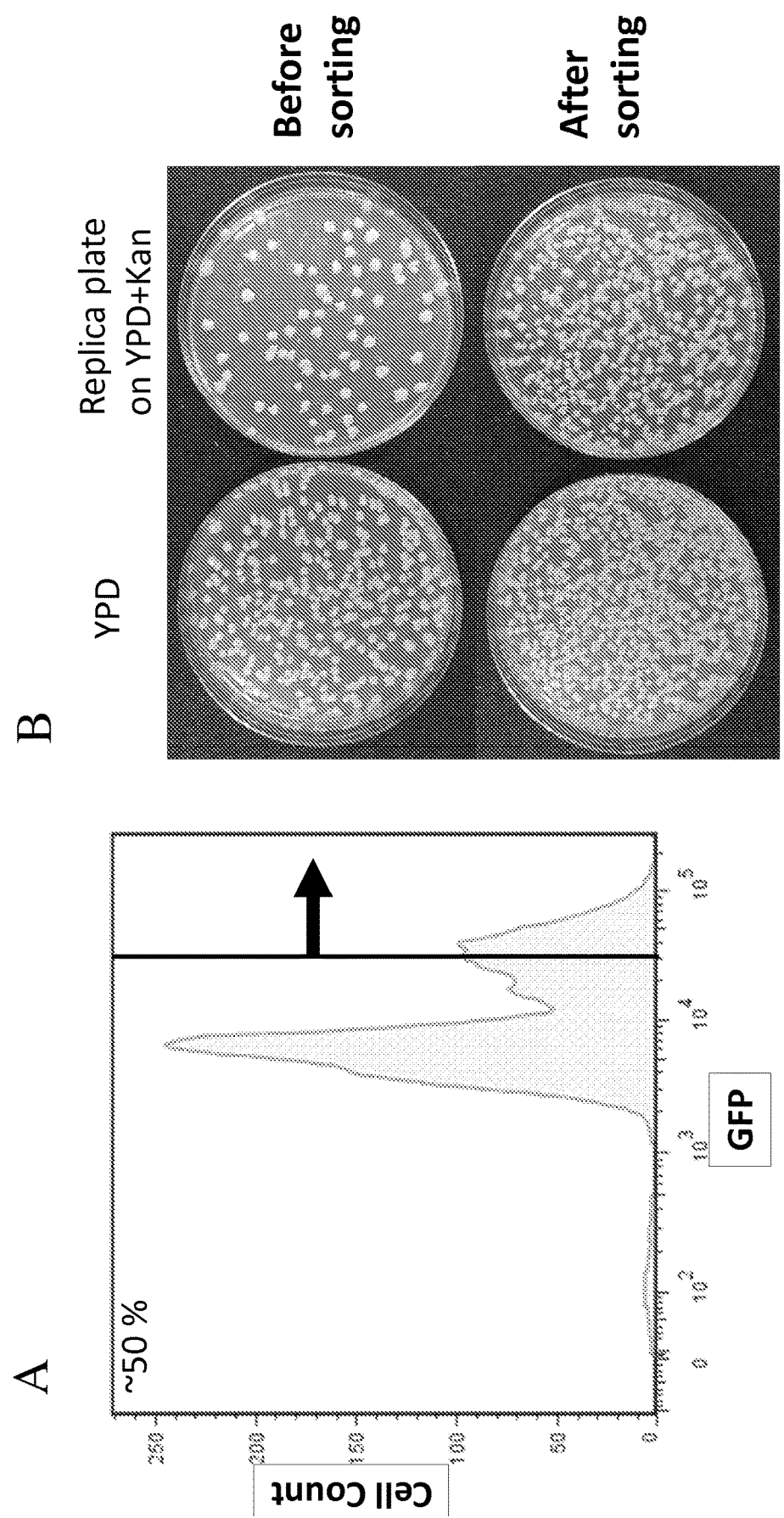
FIGS. 12A and 12B depict cell sorting by flow cytometry as a method to enrich populations of cells that have increased metabolic flux through leucine biosynthesis based on biosensor expression. A kanamycin resistance marker was added to cells expressing a Leu-insensitive Leu4 mutation. A mixture of S. cerevisiae cells containing a biosensor construct was prepared containing ~50% wild-type cells, and 50% with hyperactive leucine biosynthesis (and kanamycin-resistant).

Additional reporter genes may be included in construction of the biosensor, for example antibiotic resistance genes. For the Leu3 biosensor, the kanamycin resistance cassette was added to the biosensor construct so that cells expressing the biosensor not only express the fluorescent protein reporter but also express the kanamycin resistance gene resulting in kanamycin resistant cells. This additional feature may be beneficial in enriching cell populations that highly express the biosensor culture from those that do not express the biosensor or that express the biosensor to a lower level. As demonstrated in FIG. 12, a mixture of S. cerevisiae cells containing a biosensor construct was prepared containing ~50% wild-type cells and ~50% cells with hyperactive leucine biosynthesis (and kanamycin-resistance). Flow cytometry analysis visualized the two distinct cell populations based on intensity of expression of the fluorescent reporter. Individual populations with the desired phenotype can be FACS sorted and collected for further analysis or other methods. Following FACS sorting for cells that highly expressed the reporter, the culture was plated on solid YPD medium and replica plated onto medium containing kanamycin. As presented in FIG. 12B, following cell sorting ~90% of the cells were kanamycin resistant, compared to only ~50% before sorting. These results indicate that sorting is an effective method and can be utilized to isolate the cells with the desired phenotype based on expression of the selectable marker.

Figure 13:
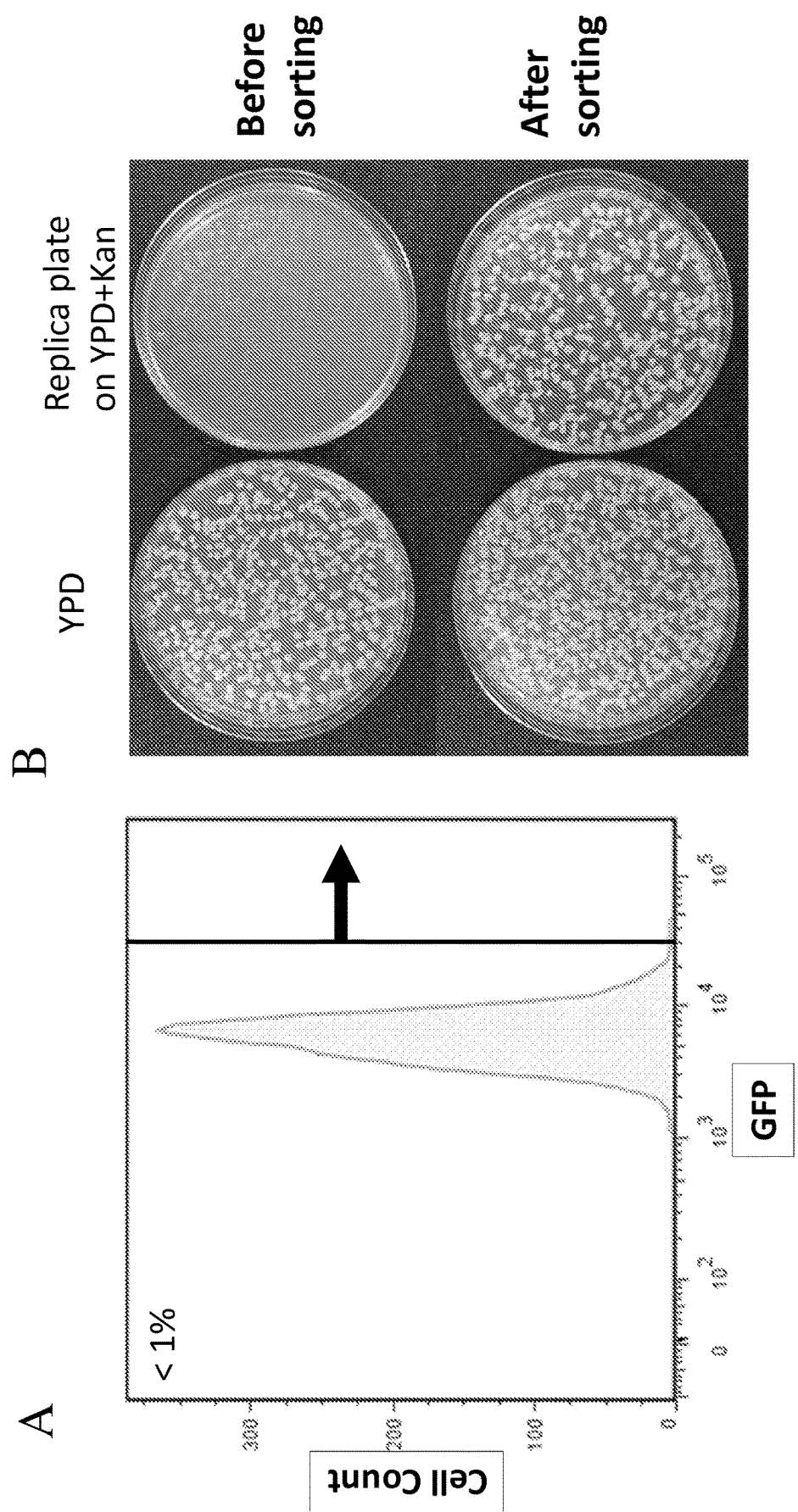
FIGS. 13A and 13B depict cell sorting by flow cytometry as a method to enrich a population of cells based on desired level of biosensor expression. As in the experiment that produced the data depicted in FIG. 12A and FIG. 12B, a kanamycin resistance marker was added to cells expressing a Leu-insensitive Leu4 mutation. In this experiment, a mixture of S. cerevisiae cells containing a biosensor construct was prepared containing >99% wild-type cells, and <1% with hyperactive leucine biosynthesis (and kanamycin-resistant).

It some embodiments, it is desirable to enrich for and expand a population of cells that display the highest level of desired phenotype, for example increased expression and activity of the reporter protein indicative of the highest production of the desired product. This can be achieved by cell sorting and collecting the desired cells. As in the experiment performed to produce the data in FIG. 12, a kanamycin resistance marked was added to the biosensor in cells expressing a leucine-insensitive Leu4 mutation. However, in this case, a mixture of S. cerevisiae cells was prepared containing >99% wild-type cells and <1% cells with hyperactive leucine biosynthesis (and kanamycin-resistance). The cells with the highest GFP expression were selected and collected (FIG. 13A). Following FACS sorting, the culture was plated on solid YPD medium and replica plated onto medium containing kanamycin. As presented in FIG. 13B, prior to sorting, no colonies grew on the medium containing kanamycin, likely due to the extremely low abundance of kanamycin resistant cells in the culture. Following enrichment, ~90% of the cells grown on YPD also grew when replica plated onto medium containing kanamycin, indicating the enrichment method is effective in collecting and amplifying desired cells from a larger population. Identification and selection of this small population would be very difficult using low throughput methods like microscopy or simply plating on solid medium. By flow cytometry and FACS sorting, this population can be collected and amplified for further methods including mutagenesis.

Although use of the Leu3 biosensor is described in detail herein, metabolic flux biosensors can be designed using many nuclear receptor-like transcription factors. An important functional consideration is the transcription factor binds a metabolite, for example a metabolite intermediate, that changes the activator/repressor state of the transcription factor to regulate expression of a selectable marker, as shown in FIG. 2 of Sellick and Reece, *Trends Biochem Sci.* 2005 July; 30(7):405-12. An exemplary list of activators and metabolic inducers are provided in FIG. 14.

Example 5

Identification of Leu⁻-Leu4 Mutants

Figure 15:
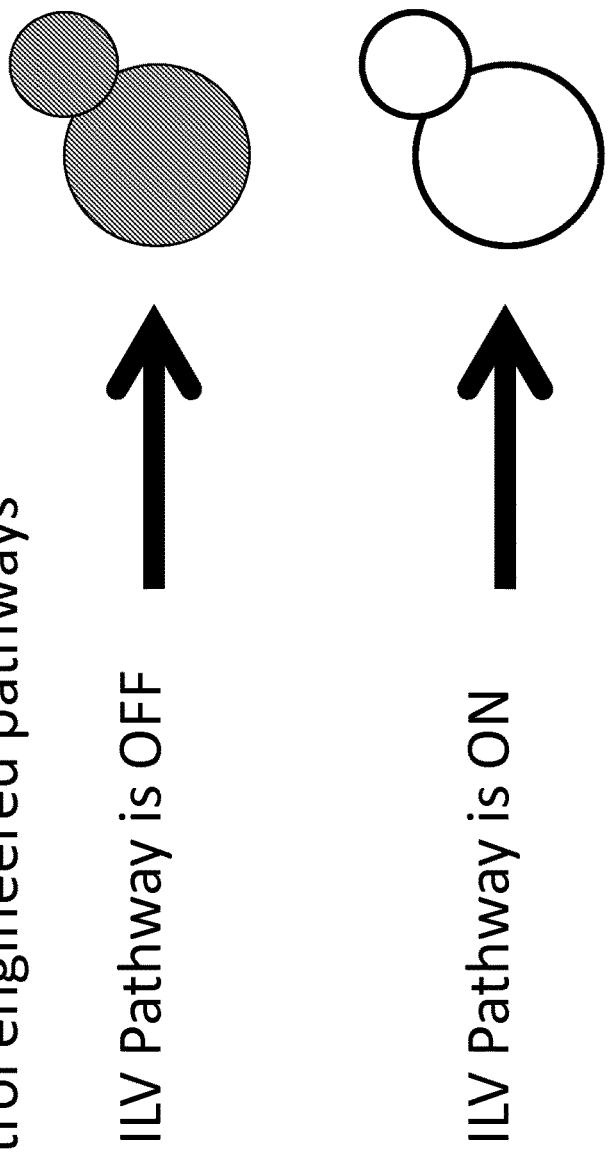
FIG. 15 presents exemplary applications for which metabolic flux biosensors may be utilized. A general schematic is shown depicting a screen using a biosensor containing a selectable marker (in this case a colorimetric or fluorescent protein). When the exemplary ILV pathway is not active, the cells display a specific phenotype, in this case appearing dark gray. When the ILV pathway is activated (i.e., by conditions of the screen), the cells display a distinguishable phenotype, in this case appearing white.

Biosensors described herein can be utilized to identify factors, including for example proteins, mutations, small molecules and culture conditions that influence production of the desired product. In the exemplary Leu3 biosensor that provides a quantifiable measure of α-IPM production as a proxy for alcohol production, further genes, mutations or conditions that up-regulate BCA synthesis and, in doing so, boost heavy alcohol production can be identified. Exemplary applications are depicted in FIG. 15.

After the surprising success in achieving a α-IPM-responsive Leu3 biosensor with a large dynamic range, S. cerevisiae strains encoding the Leu3 biosensor are subjected to unbiased mutagenesis by known methods (e.g., by transposon mutagenesis, chemical mutagenesis, etc.). Following mutagenesis, cells are recovered in nutrient-rich medium, then subjected to culture conditions in which maximal dynamic range of the biosensor activity is achieved (i.e., addition of 100 mM α-IPM to the culture). Cells are sorted by flow cytometry/FACS methods and collected for sequencing to identify the mutations that influenced biosensor expression and thus may affect alcohol production.

Figure 16:
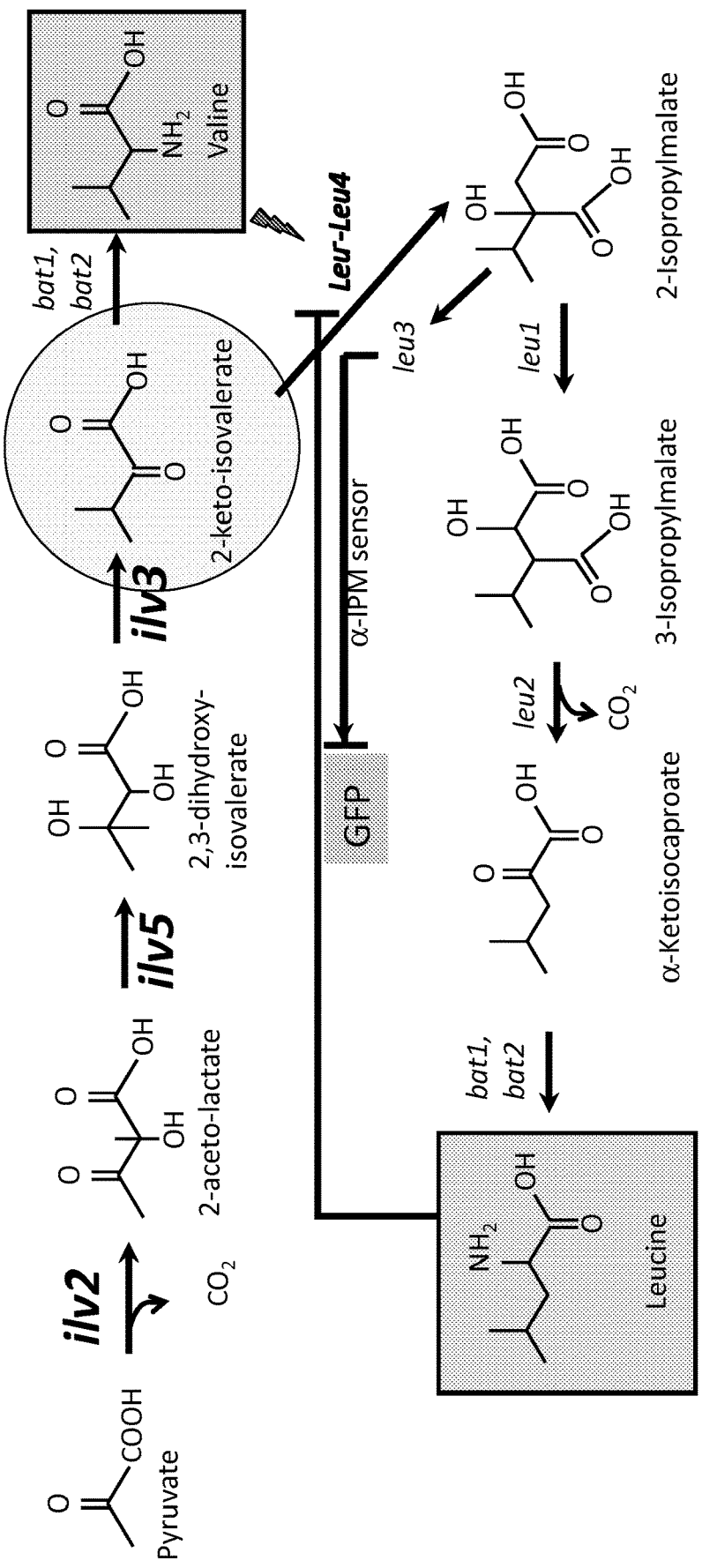
FIG. 16 shows a schematic for screening for leucine-insensitive Leu4 mutant proteins. The nucleotide sequence encoding Leu4 is mutagenized (e.g., by error-prone PCR) and introduced into S. cerevisiae strains containing the Leu3 biosensor. Activity of the mutant proteins can be assessed in the presence or absence of leucine by detection of the selectable marker, in this case GFP, for example by methods presented FIGS. 3 and 11.

Upon identification of proteins that affect production of the desired metabolite, further targeted mutagenesis can be performed on proteins in the metabolic pathway of interest to further increase production of the metabolite. For example, several genes involved in the branched chain amino acid biosynthetic pathway or its regulation, shown in FIG. 16, are targeted. Specifically, Leu4 was identified as a critical factor responsible for production of α-IPM which is an essential intermediate of the leucine and isopentanol pathways. Targeted mutagenesis of the Leu4 protein is performed by methods such as error-prone PCR. The generated libraries are used to transform strains containing the Leu3 biosensor, and the transformants are screened by fluorescence imaging, or by FACS sorting. The mutant alleles in the strains with highest fluorescence are identified by sequencing methods to identify the mutations that influence product synthesis. Mutations are then incorporated into heavy alcohol hyper-producing strains to further improve their productivity.

In addition or alternatively to mutagenesis methods, protein activity can be inhibited or modulated by subjecting cells to single-chain antibody fragments (e.g. VHH, Nanobodies). Alpacas are immunized with whole yeast protein or with purified enzymes (i.e., Pdc1p, Pdc5p) involved in ethanol fermentation. Heavy chain variable domains (VHH) are cloned from immunized alpacas and assembled into libraries. These libraries then are transformed with recombinant nucleic acid constructs containing the metabolic flux biosensor. Once expressed in the yeast cells, the VHH interacts with its specific antigen comprising a portion of a yeast protein. Cells are screened for those that have physiological effects, such as enhanced biosensor expression indicating increased production of a desired product. VHH or Nanobodies are able to inhibit or disrupt function of proteins that may be otherwise essential and would not be identified by other mutagenesis methods or may have other activities that benefit the engineered phenotype. These positive mutants are assessed for hyperactive branched chain amino acid biosynthesis and increased heavy alcohol productivity. The most interesting strains are genetically dissected and sequenced to identify the underlying mutations responsible for their enhanced traits.

Example 6

Identification of Val$^-$-ILV6 Mutants

Figure 17:
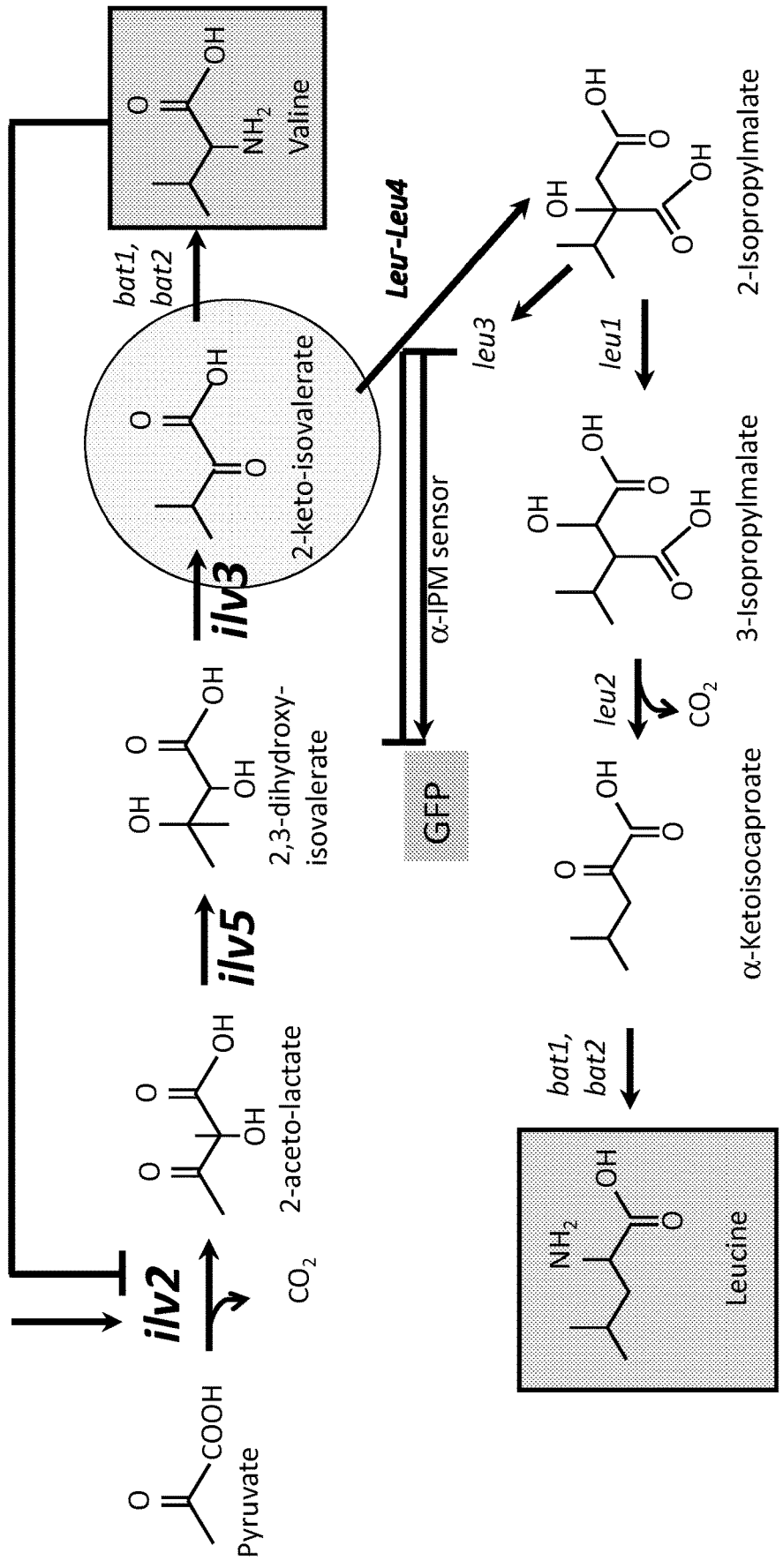
FIG. 17 shows a schematic for screening for valine-insensitive Ilv6 mutant proteins. Similar to the screening method presented in FIG. 16, the nucleotide sequence encoding Ilv6 is mutagenized (e.g., by error-prone PCR) and introduced into S. cerevisiae strains containing a Leu3 biosensor. Activity of the mutant proteins can be assessed in the presence and absence of valine by detection of the selectable marker, in this case GFP, for example by methods presented FIGS. 3 and 11.

To further optimize metabolic flux through a specific biosynthetic pathway in order to modulate production of a desired product, activity of upstream enzymes can be optimized. Using the branched chain amino acid (BCA) pathway with the goal of achieving increased alcohol production, an exemplary upstream enzyme for further optimization is Ilv6. As presented in FIG. 17, Ilv6 stimulates activity of Ilv2 that catalyzes the conversion of pyruvate into 2-aceto-lactate that is required for the BCA pathway. Ilv6 can stimulate Ilv2 activity up to 7-fold, though Ilv6 also confers valine sensitivity to Ilv2, such that in the presence of valine Ilv2 is inactivated and the pathway, including alcohol synthesis, is inhibited. 2-Aceto-lactate is an intermediate that is further processed to serve as a substrate for Leu4 and α-IPM production, thus the Leu3 biosensor described in Examples 1 and 2 may also be used to assess activity of Ilv6.

Similar to the optimization steps described in detail in Examples 1, 2 and 5 for Leu4, Ilv6 can also be mutated to reduce or eliminate valine sensitivity but retain the ability to stimulate Ilv2 and thus allow the pathway to produce the desired metabolite products despite the presence of valine. A schematic depicting a screen for Ilv6 mutants that may influence alcohol production is presented in FIG. 17. Ilv6 is mutated by any method known in the art including error-prone mutagenesis. The mutated Ilv6 proteins are expressed in S. cerevisiae strains containing the Leu3 biosensor with a selectable marker, in this case GFP, as described previously. Activity of the mutant Ilv6 proteins is assessed both in the presence or absence of valine by detection of GFP by methods including flow cytometry and fluorescence microscopy. S. cerevisiae strains that display the desired phenotype can be selected for amplification and sequencing to identify the Ilv6 mutation.

Example 7

Biosensor Constructs

The biosensors described herein may include components on one or more recombinant nucleic acid constructs such as plasmids. As exemplary constructs, herein are described constructs useful as Leu3 biosensors.

Minimally the biosensor construct has a selectable marker, such as a reporter gene encoding a fluorescent protein, operably linked to a promoter that contains a UAS bound by Leu3 protein. The promoter can be a promoter that is natively activated (or repressed) by Leu3, or a synthetic promoter containing 1, 2, 3, 4, 5 or more Leu3 UASs.

The transcription factor, in this case Leu3 protein, can be expressed by the same recombinant nucleic acid construct. For example, Leu3 can be overexpressed by operably linking a constitutive promoter to LEU3 coding sequence. Thus, this type of biosensor recombinant nucleic acid construct contains both the transcription factor (in this case, Leu3) and the selectable marker for the biosensor (in this case, a Leu3-UAS containing promoter operably linked to a sequence coding for a fluorescent protein).

Various additions to or modifications of the reporter protein can be included in the biosensor. For example, the fluorescent protein sequence can be fused to a PEST sequence that increases the turnover rate of fluorescent protein. Such fusions can be included in the biosensor recombinant nucleic acid construct.

In addition a gene product that synthesizes a small-molecule regulator of the biosensor transcription factor can be include in the same recombinant nucleic acid construct. For example, in this case a sequence encoding Leu4 protein, which converts alpha-ketoisovalerate to alpha-isopropylmalate, can be placed under control of a constitutive promoter to remove its regulation by LEU3. The Leu4 sequence can encode a Leu4 mutant protein, such as one that is insensitive to leucine inhibition, to bypass product inhibition of the biosensor.

Figure 18:
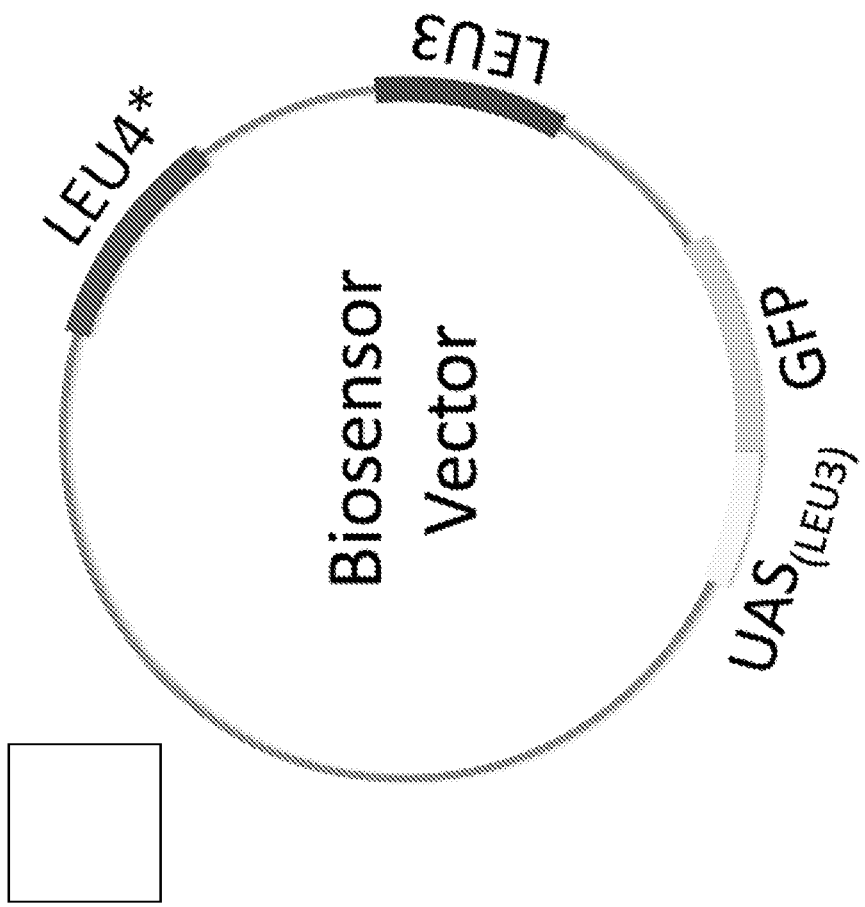
FIG. 18 shows an exemplary metabolic flux biosensor recombinant nucleic acid construct including a reporter gene (encoding GFP) driven by a promoter containing a UAS for Leu3, an optional sequence coding for Leu3, and an optional sequence coding for a leucine-insensitive Leu4 mutant (LEU4*).

An example of a biosensor construct containing all of the aforementioned elements is depicted in FIG. 18.

Example 8

Monitoring Isobutanol Production Using Biosensor Constructs

As described above, α-KIV is a direct precursor of isobutanol and is the substrate of Leu4. Yeast cells can be metabolically stimulated to up-regulate the BCA biosynthetic pathway by α-KIV supplementation of the culture medium. To determine whether the biosensor constructs are able to monitor BCA biosynthesis, yeast strains either expressing wild type LEU4 or leucine-insensitive Leu4 mutation and a biosensor construct (Construct A (FIG. 20A) or Construct B (FIG. 20B)) were grown in 10 ml minimal media and 2% glucose and metabolically stimulated to up-regulate their BCA biosynthetic pathway by supplementing the culture media with α-KIV. Cell fluorescence was measured during exponential cell growth phase. Isobutanol levels were measured at the stationary phase of each fermentation using HPLC with an Aminex HPX-87H ion-exchange column (Bio-Rad) with a mobile phase of 5 mM H2SO4 and a refractive index detector (RID).

Figure 20:
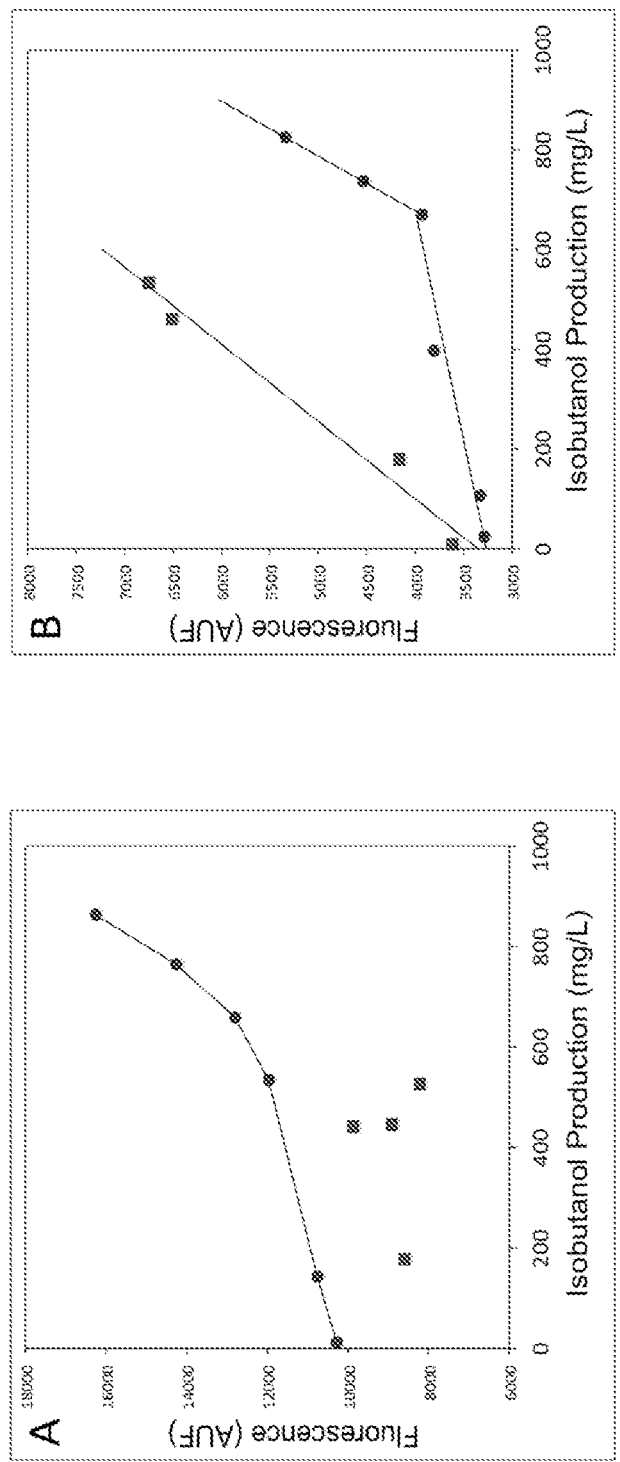
FIGS. 20A and 20B show fluorescence signals from the biosensor constructs correlate with isobutanol production.

As shown in FIGS. 20A and 20B, fluorescence signals from both biosensor Construct A (FIG. 20A) and biosensor Construct B (FIG. 20B) correlated to the isobutanol produced by the same cells carrying those biosensors. In these experiments, yeast cells carrying various biosensors were induced to increase production of isobutanol by supplementing the medium with α-KIV. This manipulation can serve as a model for conditions in which isobutanol production is elevated due to presence of, for example, particular mutation(s), deletion or overexpression of particular gene(s), other genetic or environmental perturbations, or combinations thereof. These results demonstrate that the biosensors are able to identify strains that have elevated levels of isobutanol production.

Example 9

Figure 21:
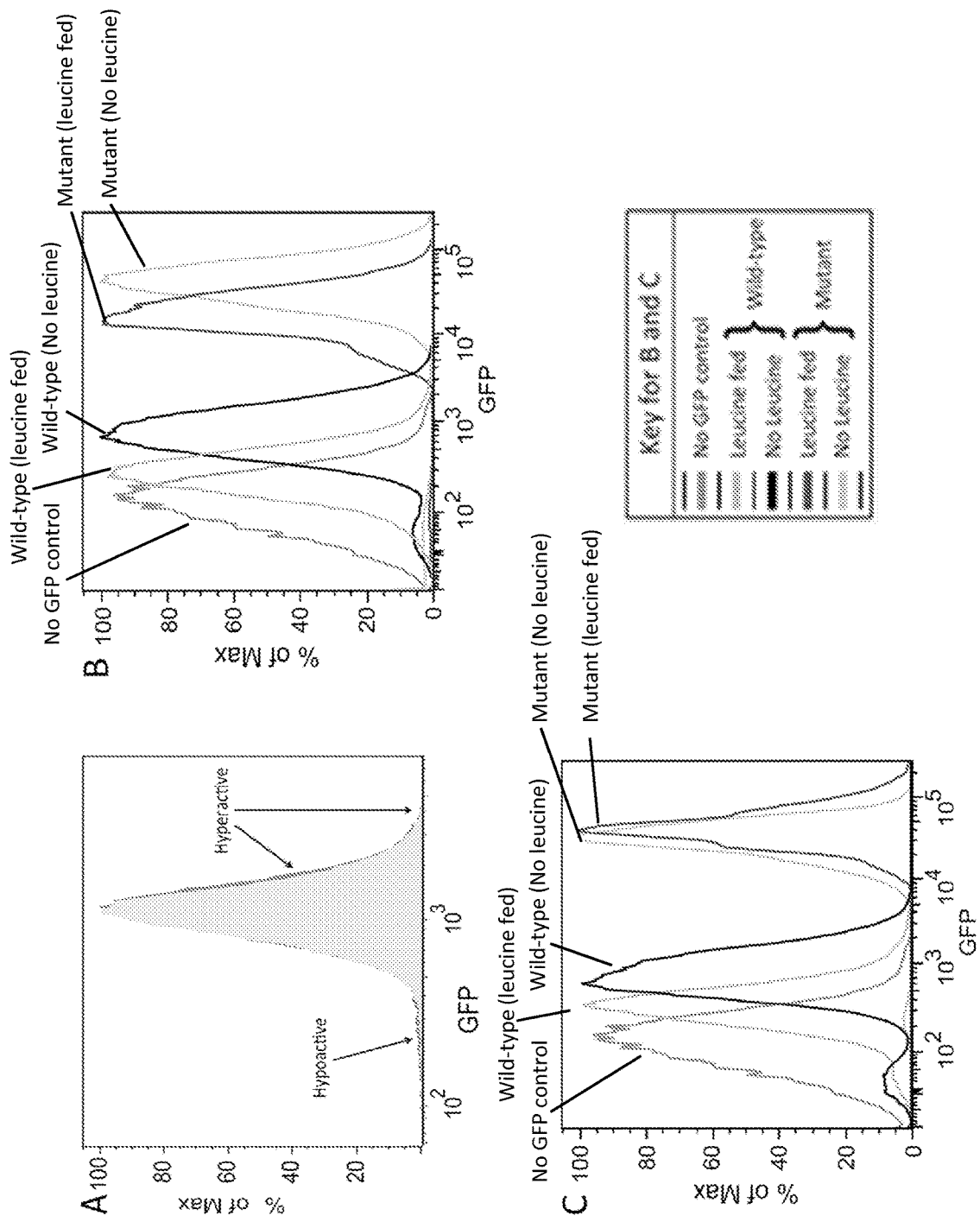
FIGS. 21A-21C show use of a Construct B Leu3 biosensor and pooled overexpression library to isolate yeast with hypo- or hyper activation of the BCA pathway.

Isolation of Yeast Mutants with Hyperactive or Leucine-Insensitive BCA Biosynthetic Pathways To identify genes and cellular networks involved in BCA biosynthesis, a screen was performed to identify genes that had an effect on the metabolic flux through the pathway. A pooled whole-genome library was prepared from yeast carrying the biosensor Construct B by transformation with the 2µ overexpression collection, in which each gene is cloned into a 2µ high-copy plasmid vector and transcribed from its native promoter (Pan, X. et al., *Molecular Cell* (2004) 16, 487-496). The Construct B biosensor, shown in FIG. 2, utilizes a Leu3-regulated promoter from Leu1 and has as a reporter a fusion protein of GFP with Leu1p. Pooled transformants were analyzed by flow cytometry and compared with the same yeast strain transformed with an empty plasmid. As demonstrated in FIG. 21A, the results indicate that some strains in the population transformed with the library have hypoactive or hyperactive metabolic activity through the BCA pathway. These populations of cells are potentially enriched with genes that cause hypo- or hyper activation of the BCA pathway.

Individual mutants with a hyperactive BCA pathway that is still sensitive to leucine inhibition (FIG. 21B) as well as individual mutants with a hyperactive BCA pathway that is insensitive to leucine (FIG. 21C) were isolated. The 2µ high-copy plasmid vector can be recovered from such strains, and the gene it carries can be identified (e.g., by sequencing), thereby identifying the gene responsible for conferring the hyperactive BCA pathway effect.

Pooled screens can likewise be performed using yeast 2µ overexpression libraries expressing a leucine-insensitive LEU4 mutation as well as with pools of other yeast collections (e.g., knockout, inducible overexpression (e.g., driven by a GAL promoter)). Appropriate methods may be used to identify the particular gene(s) that are overexpressed, deleted, or mutated in a yeast strain or yeast population of interest (e.g., a yeast strain of yeast population exhibiting increased activity of the BCA pathway). For example, a library (e.g., a yeast knockout library or overexpression library) may comprise barcodes that can be used to identify the gene(s) that are deleted or overexpressed in a given strain or enriched in a population. Alternately or additionally, deep sequencing can be used to identify the gene(s). For deep sequencing methods, PCR products from yeast cells identified in screens, as described above, can be processed and subjected to deep sequencing to identify mutations, deletions, or overexpressed genes. Any of the screens can be performed in the presence of additional nutritional or metabolic perturbations, such as in media that contain or lack various nutrients (e.g., various sugars or other carbon sources such as those mentioned herein).

Although screens using Leu3 biosensors are exemplified herein, it should be understood that similar screens can be performed using other metabolic flux biosensors, e.g., to identify genes and/or mutations that may influence activity of a metabolic pathway of interest and/or production of a desired product.

The indefinite articles "a" and "an," as used herein in the specification and in the claims, unless clearly indicated to the contrary, should be understood to mean "at least one."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements).

It should also be understood that, unless clearly indicated to the contrary, in any methods claimed herein that include more than one step or act, the order of the steps or acts of the method is not necessarily limited to the order in which the steps or acts of the method are recited.

All references (e.g., published journal articles, books, etc.), patents and patent applications disclosed herein are incorporated by reference with respect to the subject matter for which each is cited, which, in some cases, may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A cell comprising:
 a recombinant nucleic acid construct comprising a promoter operably linked to a selectable marker, wherein the promoter is regulated by a nuclear receptor-like transcription factor, the activity of which is regulated by α-isopropylmalate (α-IPM);
  wherein the cell expresses or is engineered to express the nuclear receptor-like transcription factor, which regulates the selectable marker depending on the presence or level of the α-IPM, and
  wherein the cell comprises a leucine-insensitive LEU4 mutant from S. cerevisiae that produces the α-IPM and has a mutation or deletion of amino acid Ser547, a deletion of amino acids 411-619, a deletion of amino acids 424-619, a mutation of Gly514 or Gly516 to aspartic acid, a mutation of Ala552 to threonine, a mutation of Glu540 to lysine, a mutation of His541 to proline, a mutation of Ser519 to threonine, or a mutation of Asp578 to tyrosine.

2. The cell of claim 1, wherein the nuclear receptor-like transcription factor is LEU3.

3. The cell of claim 1, wherein the promoter is a promoter regulated in vivo by the nuclear receptor-like transcription factor or wherein the promoter is an engineered synthetic promoter.

4. The cell of claim 1, wherein the selectable marker is a reporter gene that encodes a fluorescent protein or a luminescent protein, an auxotrophic marker or a gene that confers temperature sensitivity, reduced temperature sensitivity in a temperature sensitive strain, colony color, colony morphology, resistance to an antibiotic, resistance to a toxin or resistance to a toxic condition.

5. The cell of claim 1, wherein the cell is a fungal cell, a yeast cell; a bacterial cell; an archaeal cell; or a plant cell.

6. The cell of claim 1, wherein the cell is engineered or selected to produce or have increased production of a molecule of interest.

7. The cell of claim 1, wherein the nuclear receptor-like transcription factor is LEU3 and wherein the promoter is a LEU1, ILV2, LEU4, BAP2, BAT2 or GDH1 promoter.

8. The cell of claim 1, wherein the cell overexpresses one or more genes in a metabolic pathway.

9. The cell of claim 1, wherein the cell expresses one or more genes from a different organism, or a gene involved in the synthesis of a molecule of interest.

10. The cell of claim 1, wherein the cell comprises a deletion or mutation of one or more genes, or wherein the nuclear receptor-like transcription factor is one that affects a metabolic pathway and the one or more genes that are deleted or mutated are in a competing metabolic pathway.

11. The cell of claim 1, wherein the cell has increased uptake of a precursor of a molecule of interest, decreased export of a molecule of interest, or increased export of a molecule of interest relative to a control cell.

12. The cell of claim 1, wherein the cell is selected or engineered to be resistant to a molecule of interest or intermediates in or byproducts of synthesis of the molecule of interest.

13. The cell of claim 1, wherein the selectable marker comprises a peptide sequence that is rich in proline (P), glutamic acid (E), serine (S), and threonine (T) (PEST sequence).

14. The cell of claim 1, wherein the cell further comprises a factor to be screened, which comprises one or more genes or gene products that is/are added to the cell, mutated in the cell, overexpressed or activated in the cell, reduced in expression or activity in the cell or deleted from the cell.

15. The cell of claim 1, wherein the leucine-insensitive LEU4 mutant has a mutation or deletion of amino acid Ser547.

16. The cell of claim 1, wherein the leucine-insensitive LEU4 mutant has a deletion of amino acids 411-619 or a deletion of amino acids 424-619.

17. The cell of claim 1, wherein the leucine-insensitive LEU4 mutant has a mutation of Gly514 or Gly516 to aspartic acid or a mutation of Ser519 to threonine.

18. The cell of claim 1, wherein the leucine-insensitive LEU4 mutant has a mutation of Ala552 to threonine.

19. The cell of claim 1, wherein the leucine-insensitive LEU4 mutant has a mutation of Glu540 to lysine, a mutation of His541 to proline.

20. The cell of claim 1, wherein the leucine-insensitive LEU4 mutant has or a mutation of Asp578 to tyrosine.

* * * * *